(12) United States Patent
Amberg et al.

(10) Patent No.: US 6,358,983 B1
(45) Date of Patent: Mar. 19, 2002

(54) HETEROCYCLICALLY SUBSTITUTED α-HYDROXYCARBOXYLIC ACID DERIVATIVES, METHOD FOR PRODUCING THE SAME AND THEIR USE AS ENDOTHELIN RECEPTOR ANTAGONISTS

(75) Inventors: Wilhelm Amberg, Schwetzingen; Rolf Jansen, Mannheim; Heinz Hillen, Hassloch; Stefan Hergenröder, Mainz; Manfred Raschack, Weisenheim; Liliane Unger, Ludwigshafen, all of (DE)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/530,382

(22) PCT Filed: Nov. 4, 1998

(86) PCT No.: PCT/EP98/07026

§ 371 Date: Apr. 27, 2000

§ 102(e) Date: Apr. 27, 2000

(87) PCT Pub. No.: WO99/25701

PCT Pub. Date: May 27, 1999

(30) Foreign Application Priority Data

Nov. 14, 1997 (DE) .......................................... 197 50 529

(51) Int. Cl.$^7$ ..................... C07D 277/34; A61K 31/425
(52) U.S. Cl. ..................... 514/367; 548/187; 548/213; 548/221; 548/230; 548/243; 548/165; 514/369; 514/372; 514/375; 514/376; 514/380
(58) Field of Search .................. 548/187, 165, 548/230, 221, 213, 243; 514/369, 362, 375, 326, 372, 380

(56) References Cited

FOREIGN PATENT DOCUMENTS

| DE | 19533023 | 4/1996 |
|----|----------|--------|
| WO | 96 11914 | 4/1996 |

*Primary Examiner*—Robert Gerstl
(74) *Attorney, Agent, or Firm*—Keil & Weinkauf

(57) ABSTRACT

The present invention relates to carboxylic acid derivatives of the formula I

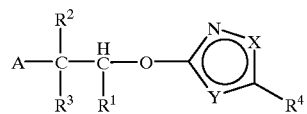

I the substituents having the meanings explained in the description, preparation and use as endothelin receptor antagonists.

5 Claims, No Drawings

HETEROCYCLICALLY SUBSTITUTED α-HYDROXYCARBOXYLIC ACID DERIVATIVES, METHOD FOR PRODUCING THE SAME AND THEIR USE AS ENDOTHELIN RECEPTOR ANTAGONISTS

The present invention relates to novel carboxylic acid derivatives, their preparation and use.

Endothelin is a peptide constructed from 21 amino acids, which is synthesized and released by vascular endothelium. Endothelin exists in three isoforms, ET-1, ET-2 and ET-3. In the following text, "endothelin" or "ET" designates one or all isoforms of endothelin. Endothelin i s a potent vasoconstrictor and has a strong effect on the vascular tone. It is known that this vasoconstriction is caused by the binding of endothelin to its receptor (Nature, 332 (1988), 411–415; FEBS Letters, 231 (1988), 440–444 and Biochem. Biophys. Res. Commun., 154 (1988), 868–875).

Increased or abnormal release of endothelin causes a lasting vascular contraction in peripheral, renal and cerebral blood vessels, which can lead to diseases. As reported in the literature, endothelin is involved in a number of diseases. These include: hypertension, acute myocardial infarct, pulmonary hypertension, Raynaud's syndrome, cerebral vasospasms, stroke, benign prostate hypertrophy, atherosclerosis, asthma and prostate cancer (J. Vascular Med. Biology 2 (1990), 207, J. Am. Med. Association 264 (1990), 2868, Nature 344 (1990), 114, N. Engl. J. Med. 322 (1989), 205, N. Engl. J. Med. 328 (1993), 1732, Nephron 66 (1994), 373, Stroke 25 (1994), 904, Nature 365 (1993), 759, J. Mol. Cell. Cardiol. 27 (1995), A234; Cancer Research 56 (1996), 663, Nature Medicine 1 (1995), 944).

At least two endothelin receptor subtypes, ETA and ETB receptors, have at present been described in the literature (Nature 348 (1990), 730, Nature 348 (1990), 732). Accordingly, substances which inhibit the binding of endothelin to one or both receptors should antagonize physiological effects of endothelin and therefore be useful pharmaceuticals.

It is an object of the present invention to provide endothelin receptor antagonists which bind to the $ET_A$ and/or the $ET_B$ receptor.

We have found that this object is achieved by heterocyclically substituted a-hydroxycarboxylic acid derivatives of the formula I

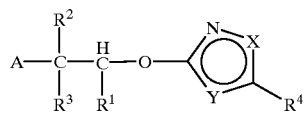

I $R_1$ being tetrazole or a group

where R has the following meanings:

a) a radical $OR^5$, where $R^5$ is:
hydrogen, the cation of an alkali metal, the cation of an alkaline earth metal, a physiologically tolerable organic ammonium ion such as tertiary $C_1$–$C_4$-alkylammonium or the ammonium ion;
$C_3$–$C_8$-cycloalkyl, $C_1$–$C_8$-alkyl, $CH_2$-phenyl, which can be substituted by one or more of the following radicals: halogen, nitro, cyano, $C_1$–$C_4$-alkyl, $C_1$–$C_4$-haloalkyl, hydroxyl, $C_1$–$C_4$-alkoxy, mercapto, $C_1$–$C_4$-alkylthio, amino, $NH(C_1$–$C_4$-alkyl), $N(C_1$–$C_4$-alkyl)_2$;
a $C_3$–$C_8$-alkenyl or a $C_3$–$C_8$-alkynyl group, it being possible for these groups for their part to carry one to five halogen atoms;
$R^5$ can furthermore be a phenyl radical which can carry one to five halogen atoms and/or one to three of the following radicals: nitro, cyano, $C_1$–$C_4$-alkyl, $C_1$–$C_4$-haloalkyl, hydroxyl, $C_1$–$C_4$-alkoxy, mercapto, $C_1$–$C_4$-alkylthio, amino, $NH(C_1$–$C_4$-alkyl), $N(C_1$–$C_4$-alkyl)_2$.

b) a 5-membered heteroaromatic linked via a nitrogen atom, such as pyrrolyl, pyrazolyl, imidazolyl or triazolyl, which can carry one or two halogen atoms, or one or two $C_1$–$C_4$-alkyl or one or two $C_1$–$C_4$-alkoxy groups.

c) a group

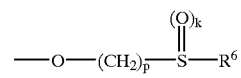

where k can assume the values 0, 1 or 2, p the values 1, 2, 3 or 4 and $R^6$ is
$C_1$–$C_4$-alkyl, $C_3$–$C_8$-cycloalkyl, $C_3$–$C_8$-alkenyl, $C_3$–$C_8$-alkynyl or phenyl, which can be mono- to trisubstituted by: halogen, nitro, cyano, $C_1$–$C_4$-alkyl, hydroxyl, $C_1$–$C_4$-alkoxy, $C_1$–$C_4$-alkylthio, amino, $NH(C_1$–$C_4$-alkyl), $N(C_1$–$C_4$-alkyl)_2$, mercapto.

d) a radical

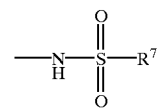

where $R^7$ is:
$C_1$–$C_4$-alkyl, $C_3$–$C_8$-alkenyl, $C_3$–$C_8$-alkynyl, $C_3$–$C_8$-cycloalkyl, it being possible for these radicals to carry a $C_1$–$C_4$-alkoxy, $C_1$–$C_4$-alkylthio and/or a phenyl radical as mentioned under c);
$C_1$–$C_4$-haloalkyl or phenyl, which can be substituted as mentioned under c).

The other substituents have the following meanings:
A is $NR^8R^9$, azido, $OR^{10}$, $SR^{10}$ or $C_1$–$C_4$-alkyl.
X is oxygen, sulfur, $CR^{11}$ or $NR^{12}$; with the proviso that if $X=CR^{11}$, then Y=oxygen or sulfur or $NR^{14}$.
Y is oxygen, sulfur, $CR^{13}$ or $NR^{14}$; with the proviso that if Y=oxygen or sulfur or $NR^{14}$, then $X=CR^{11}$.
$R^2$ and $R^3$ (which can be identical or different):
are phenyl or naphthyl, which can be substituted by one or more of the following radicals: halogen, nitro, cyano, hydroxyl, mercapto, $C_1$–$C_4$-alkyl, $C_2$–$C_4$-alkenyl, $C_2$–$C_4$-alkynyl, $C_1$–$C_4$-haloalkyl, $C_1$–$C_4$-alkoxy, phenoxy, $C_1$–$C_4$-haloalkoxy, $C_1$–$C_4$-alkylthio, amino, $NH(C_1$–$C_4$-alkyl), $N(C_1$–$C_4$-alkyl)_2$ or phenyl, which can be mono- or polysubstituted, e.g. mono- to trisubstituted, by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio; or
phenyl or naphthyl, which are connected to one another in the ortho-position via a direct bond, a methylene, ethylene or ethenylene group, an oxygen or sulfur atom or an $SO_2$, NH or $N(C_1$–$C_4$-alkyl) group;

$C_5$–$C_6$-cycloalkyl, it being possible for these radicals in each case to be mono- or polysubstituted by: halogen, hydroxyl, mercapto, carboxyl, nitro, cyano, $C_1$–$C_4$-alkyl, $C_2$–$C_4$-alkenyl, $C_2$–$C_4$-alkynyl, $C_1$–$C_4$-alkoxy, $C_1$–$C_4$-alkylthio, $C_1$–$C_4$-haloalkoxy.

and $R^{11}$ (which can be identical or different):

are hydrogen, halogen, $C_1$–$C_4$-alkoxy, $C_1$–$C_4$-haloalkoxy, $C_3$–$C_6$-alkenyloxy, $C_3$–$C_6$-alkynyloxy, $C_1$–$C_4$-alkylthio, $C_1$–$C_4$-alkylcarbonyl, $C_1$–$C_4$-alkoxycarbonyl, hydroxyl, $NH_2$, $NH(C_1$–$C_4$-alkyl), $N(C_1$–$C_4$-alkyl)$_2$; p2 $C_1$–$C_4$-alkyl, $C_2$–$C_4$-alkenyl, $C_2$–$C_4$-alkynyl, it being possible for these radicals to be substituted by halogen, hydroxyl, mercapto, carboxyl, cyano;

or $CR^4$, together with $CR^{11}$, forms a 5- or 6-membered alkylene or alkenylene ring which can be unsubstituted or substituted, and in which in each case one or more methylene groups can be replaced by oxygen, sulfur, —NH or —N($C_1$–$C_4$-alkyl).

$R^8$ is hydrogen, $C_1$–$C_8$-alkyl, $C_3$–$C_8$-alkenyl or $C_3$–$C_8$-alkynyl, $C_1$–$C_5$-alkylcarbonyl, it being possible for these radicals in each case to be mono- or polysubstituted by: halogen, hydroxyl, mercapto, carboxyl, nitro, amino, cyano, $C_1$–$C_4$-alkoxy, $C_3$–$C_6$-alkenyloxy, $C_3$–$C_6$-alkynyloxy, $C_1$–$C_4$-alkylthio, $C_1$–$C_4$-haloalkoxy, $C_1$–$C_4$-alkoxycarbonyl, $C_3$–$C_8$-alkylcarbonylalkyl, NH($C_1$–$C_4$-alkyl), N($C_1$–$C_4$-alkyl)$_2$, $C_3$–$C_8$-cycloalkyl, phenoxy or phenyl, it being possible for the aryl radicals mentioned for their part to be mono- or polysubstituted, e.g. mono- to trisubstituted, by halogen, hydroxyl, mercapto, carboxyl, nitro, cyano, $C_1$–$C_4$-alkyl, $C_1$–$C_4$-haloalkyl, $C_1$–$C_4$-alkoxy, $C_1$–$C_4$-haloalkoxy, amino, NH($C_1$–$C_4$-alkyl), N($C_1$–$C_4$-alkyl)$_2$, phenyl or $C_1$–$C_4$-alkylthio;

phenyl or naphthyl, which in each case can be substituted by one or more of the following radicals: halogen, nitro, cyano, hydroxyl, amino, $C_1$–$C_4$-alkyl, $C_1$–$C_4$-haloalkyl, $C_1$–$C_4$-alkoxy, $C_1$–$C_4$-haloalkoxy, phenoxy, $C_1$–$C_4$-alkylthio, NH($C_1$–$C_4$-alkyl), N($C_1$–$C_4$-alkyl)$_2$, dioxomethylene or dioxoethylene;

$C_3$–$C_8$-cycloalkyl, it being possible for these radicals in each case to be mono- or polysubstituted by: halogen, hydroxyl, mercapto, carboxyl, nitro, cyano, $C_1$–$C_4$-alkyl, $C_2$–$C_4$-alkenyl, $C_2$–$C_4$-alkynyl, $C_1$–$C_4$-alkoxy, $C_1$–$C_4$-alkylthio, $C_1$–$C_4$-haloalkoxy;

or $R^8$, together with $R^9$, forms a $C_3$–$C_7$-alkylene chain closed to give a ring, which can be mono- or polysubstituted by $C_1$–$C_4$-alkyl, $C_1$–$C_4$-alkylthio, $C_1$–$C_4$-alkoxy, $C_1$–$C_4$-haloalkyl, $C_1$–$C_4$-haloalkoxy, and in which an alkylene group can be replaced by oxygen or sulfur, such as —(CH$_2$)$_4$—, —(CH$_2$)$_5$—, —(CH$_2$)$_6$—, —(CH$_2$)$_7$—, —(CH$_2$)$_2$—O—(CH$_2$)$_2$—, —(CH$_2$)$_2$—S—(CH$_2$)$_2$—.

$R^9$ is hydrogen, $C_1$–$C_4$-alkyl;

or $R^9$ is as indicated under $R^8$ linked with $R^8$ to give a ring.

$R^{10}$ is hydrogen, $C_1$–$C_8$-alkyl, $C_3$–$C_8$-alkenyl or $C_3$–$C_8$-alkynyl, it being possible for these radicals in each case to be mono- or polysubstituted by: halogen, hydroxyl, mercapto, carboxyl, nitro, amino, cyano, $C_1$–$C_4$-alkoxy, $C_3$–$C_6$-alkenyloxy, $C_3$–$C_6$-alkynyloxy, $C_1$–$C_4$-alkylthio, $C_1$–$C_4$-haloalkoxy, $C_1$–$C_4$-alkoxycarbonyl, $C_3$–$C_8$-alkylcarbonylalkyl, carboxamide, CONH($C_1$–$C_4$-alkyl), CON($C_1$–$C_4$-alkyl)$_2$, CONR$^{15}$R$^{16}$, NH($C_1$–$C_4$-alkyl), N($C_1$–$C_4$-alkyl)$_2$, $C_3$–$C_8$-cycloalkyl, heteroaryloxy or heteroaryl, which is five- or six-membered, comprising one to three nitrogen atoms and/or a sulfur or oxygen atom, phenoxy or phenyl, it being possible for all aryl radicals mentioned, for their part, to be mono- or polysubstituted, e.g. mono- to trisubstituted, by halogen, hydroxyl, mercapto, carboxyl, nitro, cyano, $C_1$–$C_4$-alkyl, $C_1$–$C_4$-alkylcarboxyl, $R^{19}$, $C_1$–$C_4$-haloalkyl, $C_1$–$C_4$-alkoxy, $C_1$–$C_4$-haloalkoxy, amino, NH($C_1$–$C_4$-alkyl), N($C_1$–$C_4$-alkyl)$_2$, phenyl or $C_1$–$C_4$-alkylthio;

phenyl or naphthyl, which in each case can be substituted by one or more of the following radicals: halogen, nitro, cyano, hydroxyl, amino, $C_1$–$C_4$-alkyl, $C_1$–$C_4$-haloalkyl, $C_1$–$C_4$-alkoxy, $C_1$–$C_4$-haloalkoxy, phenoxy, $C_1$–$C_4$-alkylthio, NH($C_1$–$C_4$-alkyl), N($C_1$–$C_4$-alkyl)$_2$, dioxomethylene or dioxoethylene;

$C_3$–$C_8$-cycloalkyl, it being possible for these radicals in each case to be mono- to trisubstituted by: halogen, hydroxyl, mercapto, carboxyl, nitro, cyano, $C_1$–$C_4$-alkyl, $C_2$–$C_4$-alkenyl, $C_2$–$C_4$-alkynyl, $C_1$–$C_4$-alkoxy, $C_1$–$C_4$-alkylthio, $C_1$–$C_4$-haloalkoxy.

$R^{12}$ is hydrogen, $C_1$–$C_4$-alkyl; or $NR^{12}$, together with $CR^4$, forms a 5- or 6-membered alkylene or alkenylene ring which can be mono- to trisubstituted by $C_1$–$C_4$-alkyl, and in which in each case one or more methylene groups can be replaced by oxygen or sulfur.

$R^{13}$ is hydrogen, halogen, $C_1$–$C_4$-alkyl, $C_2$–$C_4$-alkenyl, it being possible for these radicals to be substituted by halogen.

$R^{14}$ is hydrogen, $C_1$–$C_4$-alkyl.

$R^{15}$ and $R^{16}$:

$R^{15}$ and $R^{16}$ together form a $C_3$–$C_7$-alkylene or $C_4$–$C_7$-alkenylene chain closed to give a ring, to which is fused a phenyl ring which can be mono- to trisubstituted by halogen, $C_1$–$C_4$-alkyl, $C_1$–$C_4$-alkylthio, $C_1$–$C_4$-alkoxy, $C_1$–$C_4$-haloalkyl, $C_1$–$C_4$-haloalkoxy, hydroxyl, carboxyl, amino.

$R^{19}$ is $C_1$–$C_4$-alkyl, $C_1$–$C_4$-alkylthio, $C_1$–$C_4$-alkoxy, which can carry one of the following radicals: hydroxyl, carboxyl, $C_1$–$C_4$-alkoxycarbonyl, amino, NH($C_1$–$C_4$-alkyl), N($C_1$–$C_4$-alkyl)$_2$, carboxamide or CON($C_1$–$C_4$-alkyl)$_2$.

The following definitions apply here and in the following text:

an alkali metal is, for example, lithium, sodium, potassium;

an alkaline earth metal is, for example, calcium, magnesium, barium;

$C_3$–$C_8$-cycloalkyl is, for example, cyclopropyl, cyclobutyl, cyclopentyl, cyclohexyl, cycloheptyl or cyclooctyl;

$C_1$–$C_4$-haloalkyl can be linear or branched, such as, for example, fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl or pentafluoroethyl;

$C_1$–$C_4$-haloalkoxy can be linear or branched, such as, for example, difluoromethoxy, trifluoromethoxy, chlorodifluoromethoxy, 1-fluoroethoxy, 2,2-difluoroethoxy, 1,1,2,2-tetrafluoroethoxy, 2,2,2-trifluoroethoxy, 2-chloro-1,1,2-trifluoroethoxy, 2-fluoroethoxy or pentafluoroethoxy;

$C_1$–$C_4$-alkyl can be linear or branched, such as, for example, methyl, ethyl, 1-propyl, 2-propyl, 2-methyl-2-propyl, 2-methyl-1-propyl, 1-butyl or 2-butyl;

$C_2$–$C_4$-alkenyl can be linear or branched, such as, for example, ethenyl, 1-propen-3-yl, 2-propen-3-yl, 1-propen-1-yl, 2-methyl-1-propenyl, 1-butenyl or 2-butenyl;

$C_2$–$C_4$-alkynyl can be linear or branched, such as, for example, ethynyl, 1-propyn-1-yl, 1-propyn-3-yl, 1-butyn-4-yl or 2-butyn-4-yl;

$C_1$–$C_4$-alkoxy can be linear or branched, such as, for example, methoxy, ethoxy, propoxy, 1-methylethoxy, butoxy, 1-methylpropoxy, 2-methylpropoxy or 1,1-dimethylethoxy;

$C_3$–$C_6$-alkenyloxy can be linear or branched, such as, for example, allyloxy, 2-buten-1-yloxy or 3-buten-2-yloxy;

$C_3$–$C_6$-alkynyloxy can be linear or branched, such as, for example, 2-propyn-1-yloxy, 2-butyn-1-yloxy or 3-butyn-2-yloxy;

$C_1$–$C_4$-alkylthio can be linear or branched, such as, for example, methylthio, ethylthio, propylthio, 1-methylethylthio, butylthio, 1-methylpropylthio, 2-methylpropylthio or 1,1-dimethylethylthio;

$C_1$–$C_4$-alkylcarbonyl can be linear or branched, such as, for example, acetyl, ethylcarbonyl or 2-propylcarbonyl;

$C_1$–$C_4$-alkoxycarbonyl can be linear or branched, such as, for example, methoxycarbonyl, ethoxycarbonyl, n-propoxycarbonyl, i-propoxycarbonyl or n-butoxycarbonyl;

$C_3$–$C_8$-alkylcarbonylalkyl can be linear or branched, e.g. 2-oxoprop-1-yl, 3-oxobut-1-yl or 3-oxobut-2-yl;

$C_1$–$C_8$-alkyl can be linear or branched, such as, for example, $C_1$–$C_4$-alkyl, pentyl, hexyl, heptyl or octyl; halogen is, for example, fluorine, chlorine, bromine, iodine.

The invention further relates to those compounds from which the compounds of the formula I can be released (prodrugs).

Preferred prodrugs are those in which the release proceeds under conditions such as prevail in certain body compartments, e.g. in the stomach, intestine, blood circulation, liver.

The invention further relates to the use of the abovementioned carboxylic acid derivatives for the production of drugs, in particular for the production of inhibitors for $ET_A$ and $ET_B$ receptors.

The compounds I and also the intermediates for their preparation, such as, for example, II, can have one or more asymmetrically substituted carbon atoms. Such compounds can be present as pure enantiomers or pure diastereomers or as a mixture thereof. The use of an enantiomerically pure compound as the active compound is preferred.

The compounds having the formula IIa in which A is $C_1$–$C_4$-alkyl, azido, $SR^{10}$ or $OR^{10}$ can be prepared as described in WO 96/11914, DE 19614533.3 or DE 19726146.9.

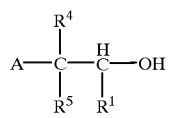

IIa

Compounds of the formula IIb where A is $SR^{10}$ or $OR^{10}$ can be obtained in enantiomerically pure form via an acid-catalyzed transetherification, such as has been described in DE 19636046.3.

Enantiomerically pure compounds of the formula II can furthermore be obtained by carrying out a classical resolution with racemic or diastereomeric compounds of the formula II using suitable enantiomerically pure bases. Suitable bases of this kind are, for example, 4-chlorophenylethylamine and the bases which are mentioned in WO 96/11914.

The compounds Ia according to the invention, where A is $C_1$–$C_4$-alkyl, azido, $SR^{10}$ or $OR^{10}$ and the other substituents have the meaning given under the formula I, can be prepared, for example, by reacting the carboxylic acid derivatives of the formula IIa, where the substituents have the given meaning, with compounds of the formula III.

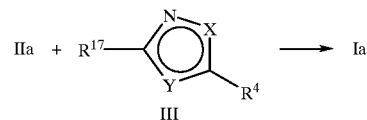

In formula III, $R^{17}$ is halogen or $R^{18}$—$SO_2$, it being possible for $R^{18}$ to be $C_1$–$C_4$-alkyl, $C_1$–$C_4$-haloalkyl or phenyl. The reaction preferably takes place in an inert solvent or diluent with addition of a suitable base, i.e. of a base which brings about a deprotonation of the intermediate IIa, in a temperature range from room temperature up to the boiling point of the solvent.

Compounds of the type Ia where $R^1$=COOH can be obtained directly in this manner if the intermediate IIa, where $R^1$ is COOH, is deprotonated using two equivalents of a suitable base and reacted with compounds of the formula III. Here too, the reaction takes place in an inert solvent and in a temperature range from room temperature up to the boiling point of the solvent.

Examples of such solvents or diluents are aliphatic, alicyclic and aromatic hydrocarbons, which in each case may or may not be chlorinated, such as, for example, hexane, cyclohexane, petroleum ether, naphtha, benzene, toluene, xylene, methylene chloride, chloroform, carbon tetrachloride, ethyl chloride and trichloroethylene, ethers, such as, for example, diisopropyl ether, dibutyl ether, methyl tert-butyl ether, propylene oxide, dioxane and tetrahydrofuran, nitrites, such as, for example, acetonitrile and propionitrile, acid amides, such as, for example, dimethylformamide, dimethylacetamide and N-methylpyrrolidone, sulfoxides and sulfones, such as, for example, dimethyl sulfoxide and sulfolane.

Compounds of the formula III are known or can be prepared in a generally known manner such as, for example: H. Erlenmeyer, G. Bischoff, Helv. Chim. Acta, 29 (1946), 280–283, G. Kjellin, J. Sandstrom, Acta Chim. Scand., 23 (1969), 2879, E. R. Buchmann, A. O. Reims, H. Sargent, J. Org. Chem., 6 (1941), 764–766, F. C. James, H. D. Krebs, Aust. J. Chem., 35 (1982), 385–391, G. R. Humphrey, S. H. B. Wright, J. Heterocyclic Chem., 26 (1989), 23.

The base used can be an alkali metal or alkaline earth metal hydride such as sodium hydride, potassium hydride or calcium hydride, a carbonate such as an alkali metal carbonate, e.g. sodium or potassium carbonate, an alkali metal or alkaline earth metal hydroxide such as sodium or potassium hydroxide, an organometallic compound such as butyllithium or an alkali metal amide such as lithium diisopropylamide or lithium amide.

Compounds of the formula IIb can be reacted similarly to the methods described in DE 19726146.9 to give the compounds Ib.

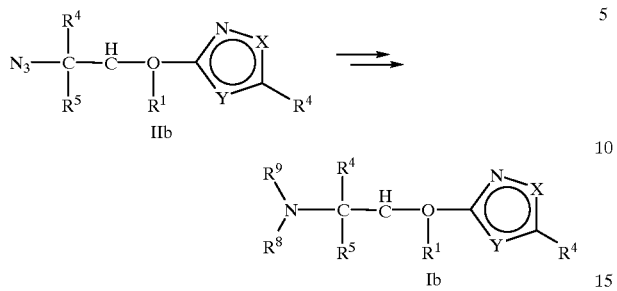

Compounds of the formula I can also be prepared by starting from the corresponding carboxylic acids, i.e. compounds of the formula I where $R^1$ is COOH, and converting these first in a customary manner into an activated form such as an acid halide, an anhydride or imidazolide and then reacting this with an appropriate hydroxyl compound $HOR^5$. This reaction can be carried out in the customary solvents and often necessitates the addition of a base, those mentioned above being suitable. These two steps can also be simplified, for example, by allowing the carboxylic acid to act on the hydroxyl compound in the presence of a dehydrating agent such as a carbodiimide.

Additionally, compounds of the formula I can also be prepared by starting from the salts of the corresponding carboxylic acids, i.e. from compounds of the formula I where $R^1$ is a group COOM, it being possible for M to be an alkali metal cation or the equivalent of an alkaline earth metal cation. These salts can be reacted with many compounds of the formula R—W, W being a customary nucleofugic leaving group, for example a halogen such as chlorine, bromine, iodine or aryl- or alkylsulfonyl which is unsubstituted or substituted by halogen, alkyl or haloalkyl, such as, for example, toluenesulfonyl and methylsulfonyl or another equivalent leaving group. Compounds of the formula R—W having a reactive substituent W are known or easy to obtain using common expert knowledge. This reaction can be carried out in the customary solvents and is advantageously carried out with addition of a base, those mentioned above being suitable.

In some cases, the use of generally known protective group techniques is necessary for preparing the compounds I according to the invention. If, for example, $R^{10}$=4-hydroxyphenyl, the hydroxyl group can first be protected as a benzyl ether, which is then cleaved at a suitable stage in the reaction sequence.

Compounds of the formula I where $R^1$ is tetrazole can be prepared as described in WO 96/11914.

With respect to the biological action, carboxylic acid derivatives of the formula I—both as pure enantiomers or pure diastereomers or as a mixture thereof—are preferred in which the substituents have the following meanings:

A is $NR^8R^9$, azido, $OR^{10}$, $SR^{10}$ or $C_1$–$C_4$-alkyl.

X is oxygen, sulfur, $CR^{11}$ or $NR^{12}$; with the proviso that if X=$CR^{11}$, then Y=oxygen or sulfur or $NR^{14}$.

Y is oxygen, sulfur, $CR^{13}$ or $NR^{14}$; with the proviso that if Y=oxygen or sulfur or $NR^{14}$, then X=$CR^{11}$.

$R^2$ and $R^3$ (which can be identical or different):
are phenyl or naphthyl, which can be substituted by one or more of the following radicals: halogen, cyano, hydroxyl, mercapto, amino, $C_1$–$C_4$-alkyl, $C_1$–$C_4$-haloalkyl, $C_1$–$C_4$-alkoxy, $C_1$–$C_4$-haloalkoxy, phenoxy, $C_1$–$C_4$-alkylthio, NH($C_1$–$C_4$-alkyl) or N($C_1$–$C_4$-alkyl)$_2$ or phenyl, which can be mono- to trisubstituted by halogen, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio; or phenyl or naphthyl, which are connected to one another in the ortho-position by a direct bond, a methylene, ethylene or ethenylene group, an oxygen or sulfur atom or an $SO_2$, NH or N($C_1$–$C_4$-alkyl) group;

$C_5$–$C_6$-cycloalkyl, it being possible for these radicals in each case to be mono- to tri-substituted by: halogen, $C_1$–$C_4$-alkyl, $C_1$–$C_4$-alkoxy, $C_1$–$C_4$-alkylthio, $C_1$–$C_4$-haloalkoxy.

$R^4$ and $R^{11}$ (which can be identical or different):
are $C_1$–$C_4$-alkyl, it being possible for these radicals to be substituted by halogen, hydroxyl;

hydrogen, halogen, $C_1$–$C_4$-alkoxy, $C_1$–$C_4$-haloalkoxy, $C_1$–$C_4$-alkylthio, hydroxyl, $NH_2$, NH($C_1$–$C_4$-alkyl), N($C_1$–$C_4$-alkyl)$_2$;

or $CR^4$, together with $CR^{11}$, forms a 5- or 6-membered alkylene or alkenylene ring which can be mono- to trisubstituted by $C_1$–$C_4$-alkyl and in which in each case one to three methylene groups can be replaced by oxygen or sulfur.

$R^8$ is hydrogen, $C_1$–$C_8$-alkyl, $C_1$–$C_5$-alkylcarbonyl, it being possible for these radicals in each case to be mono- to trisubstituted by: halogen, hydroxyl, carboxyl, amino, $C_1$–$C_4$-alkoxy, $C_1$–$C_4$-alkylthio, $C_1$–$C_4$-haloalkoxy, $C_1$–$C_4$-alkoxycarbonyl, NH($C_1$–$C_4$-alkyl), N($C_1$–$C_4$-alkyl)$_2$, $C_5$–$C_6$-cycloalkyl, phenoxy or phenyl, it being possible for the aryl radicals mentioned, for their part, to be mono- to trisubstituted by halogen, hydroxyl, $C_1$–$C_4$-alkyl, $C_1$–$C_4$-haloalkyl, $C_1$–$C_4$-alkoxy, $C_1$–$C_4$-haloalkoxy, amino, NH($C_1$–$C_4$-alkyl), N($C_1$–$C_4$-alkyl)$_2$, phenyl or $C_1$–$C_4$-alkylthio;

phenyl or naphthyl, which in each case can be mono- to trisubstituted by halogen, hydroxyl, amino, $C_1$–$C_4$-alkyl, $C_1$–$C_4$-haloalkyl, $C_1$–$C_4$-alkoxy, $C_1$–$C_4$-haloalkoxy, phenoxy, $C_1$–$C_4$-alkylthio, NH($C_1$–$C_4$-alkyl), N($C_1$–$C_4$-alkyl)$_2$, dioxomethylene or dioxoethylene;

$C_3$–$C_8$-cycloalkyl, it being possible for these radicals in each case to be mono- to trisubstituted by: halogen, $C_1$–$C_4$-alkyl, $C_1$–$C_4$-alkoxy, $C_1$–$C_4$-alkylthio, $C_1$–$C_4$-haloalkoxy;

or $R_8$, together with $R^9$, forms a $C_4$–$C_6$-alkylene chain closed to give a ring, which can be mono- to trisubstituted by $C_1$–$C_4$-alkyl, $C_1$–$C_4$-haloalkyl, and in which an alkylene group can be replaced by oxygen or sulfur, such as —$(CH_2)_4$—, —$(CH_2)_5$—, —$(CH_2)_6$—, —$(CH_2)_2$—O—$(CH_2)_2$—, —$(CH_2)_2$—S—$(CH_2)_2$—.

$R^9$ is hydrogen, $C_1$–$C_4$-alkyl;
or $R^9$ is as given under $R^8$ linked with $R^8$ to give a ring.

$R^{10}$ is hydrogen, $C_1$–$C_8$-alkyl, $C_3$–$C_8$-alkenyl or $C_3$–$C_8$-alkynyl, it being possible for these radicals in each case to be mono- to trisubstituted by: halogen, hydroxyl, mercapto, carboxyl, amino, $C_1$–$C_4$-alkoxy, $C_1$–$C_4$-alkylthio, $C_1$–$C_4$-haloalkoxy, $C_1$–$C_4$-alkoxycarbonyl, carboxamide, CONH($C_1$–$C_4$-alkyl), CON($C_1$–$C_4$-alkyl)$_2$, $CONR^{15}R^{16}$, NH($C_1$–$C_4$-alkyl), N($C_1$–$C_4$-alkyl)$_2$, $C_5$–$C_6$-cycloalkyl, phenoxy or phenyl, it being possible for the aryl radicals mentioned for their part to be mono- to trisubstituted by halogen, hydroxyl, $C_1$–$C_4$-alkyl, $C_1$–$C_4$-alkylcarboxyl, $C_1$–$C_4$-haloalkyl, $C_1$–$C_4$-alkoxy, $C_1$–$C_4$-haloalkoxy, amino, NH($C_1$–$C_4$-alkyl), N($C_1$–$C_4$-alkyl)$_2$, phenyl, $C_1$–$C_4$-alkylthio or $R^{19}$;

phenyl or naphthyl, which in each case can be mono- to trisubstituted by: halogen, hydroxyl, amino, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, NH($C_1$–$C_4$-alkyl), N($C_1$–$C_4$-alkyl)$_2$, dioxomethylene or dioxoethylene;

$C_3$–$C_8$-cycloalkyl, it being possible for these radicals in each case to be mono- to trisubstituted by: halogen, $C_1$–$C_4$-alkyl, $C_1$–$C_4$-alkoxy, $C_1$–$C_4$-haloalkyl.

$R^{12}$ is hydrogen, methyl; or
  $NR^{12}$, together with $CR^4$, forms a 5- or 6-membered alkylene ring which can be mono- to trisubstituted by methyl.

$R^{13}$ is hydrogen, halogen, $C_1$–$C_4$-alkyl, it being possible for these radicals to be mono- to trisubstituted by halogen.

$R^{14}$ is hydrogen, methyl.

$R^{15}$ and $R^{16}$:
  $R^{15}$ and $R^{16}$ together form a $C_3$–$C_7$-alkylene chain or $C_4$–$C_7$-alkenylene chain closed to give a ring, to which a phenyl ring is fused, such as 7-aza-bicyclo[4.2.0]-octa-1,3,5-triene, 2,3-dihydroindole, indole, 1,3-dihydroisoindole, 1,2,3,4-tetrahydroquinoline, 1,2,3,4-tetrahydroisoquinoline, it being possible in each case for the phenyl ring to be mono- to trisubstituted by halogen, $C_1$–$C_4$-alkyl, $C_1$–$C_4$-alkoxy, $C_1$–$C_4$-haloalkyl, $C_1$–$C_4$-haloalkoxy.

$R^{19}$ is methyl, ethyl, methoxy or ethoxy, which carry one of the following radicals: hydroxyl, carboxyl, $C_1$–$C_4$-alkoxycarbonyl, amino, NH($C_1$–$C_4$-alkyl), N($C_1$–$C_4$-alkyl)$_2$, carboxamide or CON($C_1$–$C_4$-alkyl)$_2$.

Particularly preferred compounds of the formula I (both as pure enantiomers or pure diastereomers or as a mixture thereof—are those in which the substituents have the following meanings:

A is $NR^8R^9$, azido, $OR^{10}$, $SR^{10}$ or $C_1$–$C_4$-alkyl

X is oxygen, sulfur or $CR^{11}$; with the proviso that if $X=CR^{11}$, then Y=oxygen or sulfur.

Y is oxygen, sulfur or $CR^{13}$; with the proviso that if Y=oxygen or sulfur, then $X=CR^{11}$.

$R^2$ and $R^3$ (which can be identical or different):
  are phenyl or naphthyl, which in each case can be mono- to trisubstituted by: halogen, hydroxyl, $C_1$–$C_4$-alkyl, $C_1$–$C_4$-haloalkyl, $C_1$–$C_4$-alkoxy, $C_1$–$C_4$-haloalkoxy, NH($C_1$–$C_4$-alkyl), N($C_1$–$C_4$-alkyl)$_2$, phenoxy or phenyl, which can be mono- to trisubstituted by $C_1$–$C_4$-alkyl, $C_1$–$C_4$-haloalkyl, $C_1$–$C_4$-alkoxy or $C_1$–$C_4$-haloalkoxy; or
  phenyl or naphthyl, which are connected to one another in the ortho-position via a direct bond, a methylene, ethylene or ethenylene group, an oxygen or sulfur atom or an $SO_2$, NH or N($C_1$–$C_4$-alkyl) group; cyclohexyl.

$R^4$ and $R^{11}$ (which can be identical or different):
  are hydrogen, halogen, $C_1$–$C_4$-alkyl, trifluoromethyl, hydroxymethylene, $C_1$–$C_4$-alkoxy, $C_1$–$C_4$-alkylthio, N($C_1$–$C_4$-alkyl)$_2$;
  or $CR^4$, together with $CR^{11}$, forms a 5- or 6-membered alkylene or alkenylene ring which can be mono- or disubstituted by methyl, and in which in each case a methylene group can be replaced by oxygen;

$R^8$ is hydrogen, $C_1$–$C_4$-alkyl, $C_1$–$C_4$-alkylcarbonyl, it being possible for these radicals to mono- to trisubstituted by: halogen, hydroxyl, carboxyl, amino, $C_1$–$C_4$-alkoxy, $C_1$–$C_4$-alkylthio, $C_1$–$C_4$-haloalkoxy, $C_1$–$C_4$-alkoxycarbonyl, NH($C_1$–$C_4$-alkyl), N($C_1$–$C_4$-alkyl)$_2$, $C_5$–$C_6$-cycloalkyl, phenyl, which for its part can be mono- to trisubstituted by halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio;
  phenyl which can be mono- to trisubstituted by halogen, hydroxyl, $C_1$–$C_4$-alkyl, trifluoromethyl, $C_1$–$C_4$-alkoxy, $C_1$–$C_4$-alkylthio, dioxomethylene or dioxoethylene; $C_5$–$C_6$-cycloalkyl, it being possible for these radicals in each case to be mono- to trisubstituted by: halogen, $C_1$–$C_4$-alkyl, $C_1$–$C_4$-alkoxy;

or $R^8$, together with $R^9$, forms a $C_4$–$C_6$-alkylene chain closed to give a ring, which can be mono- to trisubstituted by $C_1$–$C_4$-alkyl, $C_1$–$C_4$-haloalkyl, and in which an alkylene group can be replaced by oxygen, such as —(CH$_2$)$_4$—, —(CH$_2$)$_5$—, —(CH$_2$)$_6$—, —(CH$_2$)$_2$—O—(CH$_2$)$_2$—.

$R^9$ is hydrogen, $C_1$–$C_4$-alkyl;
  or $R^9$ is as indicated under $R^8$ linked with $R^8$ to give a ring.

$R^{10}$ is hydrogen, $C_1$–$C_4$-alkyl, it being possible for these radicals in each case to be mono- to trisubstituted by: halogen, hydroxyl, carboxyl, $C_1$–$C_4$-alkoxy, $C_1$–$C_4$-alkoxycarbonyl, carboxamide, CONH($C_1$–$C_4$-alkyl), CON($C_1$–$C_4$-alkyl)$_2$, CONR$^{15}$R$^{16}$, NH($C_1$–$C_4$-alkyl), N($C_1$–$C_4$-alkyl)$_2$, $C_5$–$C_6$-cycloalkyl, phenyl, which for its part can be mono- to trisubstituted by halogen, hydroxyl, $C_1$–$C_4$-alkyl, $C_1$–$C_4$-alkylcarboxyl, trifluoromethyl, $C_1$–$C_4$-alkoxy, NH($C_1$–$C_4$-alkyl), $R^{19}$, N($C_1$–$C_4$-alkyl)$_2$, phenyl or $C_1$–$C_4$-alkylthio;
  phenyl which can be mono- to trisubstituted by halogen, hydroxyl, $C_1$–$C_4$-alkyl, $C_1$–$C_4$-haloalkyl, $C_1$–$C_4$-alkoxy, $C_1$–$C_4$-alkylthio, NH($C_1$–$C_4$-alkyl), N($C_1$–$C_4$-alkyl)$_2$, dioxomethylene or dioxoethylene; $C_3$–$C_8$-cycloalkyl, it being possible for these radicals in each case to be mono- or polysubstituted by: halogen, $C_1$–$C_4$-alkyl, $C_1$–$C_4$-alkoxy.

$R^{13}$ is hydrogen, halogen, $C_1$–$C_4$-alkyl, trifluoromethyl.

$R^{15}$ and $R^{16}$:
  $R^{15}$ and $R^{16}$ together form a $C_3$–$C_7$-alkylene chain closed to give a ring, to which a phenyl ring is fused, such as 2,3-dihydroindole, indole, 1,3-dihydroisoindole, 1,2,3,4-tetrahydroquinoline, 1,2,3,4-tetrahydroisoquinoline, it being possible for the phenyl ring in each case to be mono- to trisubstituted by halogen, $C_1$–$C_4$-alkyl, $C_1$–$C_4$-alkoxy, hydroxyl;

$R^{19}$ is methoxy or ethoxy, which carry one of the following radicals: hydroxyl, carboxyl, $C_1$–$C_4$-alkoxycarbonyl, amino, NH($C_1$–$C_4$-alkyl), N($C_1$–$C_4$-alkyl)$_2$, carboxamide or CON($C_1$–$C_4$-alkyl)$_2$.

The compounds of the present invention offer a novel therapeutic potential for the treatment of hypertension, high pulmonary pressure, myocardial infarct, angina pectoris, arrhythmia, acute/chronic kidney failure, chronic cardiac insufficiency, renal insufficiency, cerebral vasospasms, cerebral ischemia, subarachnoid hemorrhages, migraine, asthma, atherosclerosis, endotoxic shock, endotoxin-induced organ failure, intravascular coagulation, restenosis after angioplasty and bypass operations, benign prostate hyperplasia, kidney failure or hypertension caused by ischemia and by intoxication, metastasis and growth of mesenchymal tumors such as prostate carcinoma, contrast agent-induced kidney failure, pancreatitis, gastrointestinal ulcers.

The invention further relates to combinations of endothelin receptor antagonists of the formula I and inhibitors of the renin-angiotension system. Inhibitors of the renin-angiotension system are renin inhibitors, angiotension II antagonists and angiotension-converting enzyme (ACE) inhibitors. Combinations of endothelin receptor antagonists of the formula I and ACE inhibitors are preferred.

The invention further relates to combinations of endothelin receptor antagonists of the formula I and calcium antagonists such as verapamil.

The invention further relates to combinations of endothelin receptor antagonists of the formula I and beta-blockers.

The invention further relates to combinations of endothelin receptor antagonists of the formula I and diuretics.

The invention further relates to combinations of endothelin receptor antagonists of the formula I and substances which block the action of VEGF (vascular endothelial growth factor). Such substances are, for example, antibodies directed against VEGF or specific binding proteins or alternatively low molecular weight substances which can specifically inhibit VEGF release or receptor binding.

The abovementioned combinations can be administered simultaneously or sequentially. They can be employed both in a single pharmaceutical formulation or alternatively in separate formulations. The administration form can also be different, for example the endothelin receptor antagonists can be administered orally and VEGF inhibitors parenterally.

These combination preparations are especially suitable for the treatment and prevention of hypertension and its sequelae and also for the treatment of cardiac insufficiency.

The good action of the compounds can be seen in the following experiments:

Receptor Binding Studies

For binding studies, cloned human $ET_A$ or $ET_B$ receptor-expressing CHO cells were employed.

Membrane Preparation

The $ET_A$ or $ET_B$ receptor-expressing CHO cells were proliferated in DMEM NUT MIX $F_{12}$ medium (Gibco, No. 21331-020) using 10% fetal calf serum (PAA Laboratories GmbH, Linz, No. A15-022), 1 mM glutamine (Gibco No. 25030-024), 100 U/ml of penicillin and 100 µg/ml of streptomycin (Gibco, Sigma No P-0781). After 48 hours, the cells were washed with PBS and incubated at 37° C. for 5 minutes with 0.05% trypsin-containing PBS. Neutralization with medium was then carried out and the cells were collected by centrifugation at 300×g.

For the membrane preparation, the cells were adjusted to a concentration of $10^8$ cells/ml of buffer (50 mM tris·HCL buffer, pH 7.4) and then disintegrated by means of ultrasound Branson Sonifier 250, 40–70 seconds/constant/output [sic] 20).

Binding Tests

For the $ET_A$ and $ET_B$ receptor binding test, the membranes were suspended in incubation buffer (50 mM tris HCl, pH 7.4 with 5 mM $MnCl_2$, 40 mg/ml of bacitracin and 0.2% BSA) in a concentration of 50 µg of protein per test batch and incubated at 25° C. with 25 pM [125I]-$ET_1$ ($ET_A$ receptor test) or 25 pM [125I]-$ET_3$ ($ET_B$ receptor test) in the presence or absence of test substance. The nonspecific binding was determined with $10^{-7}$ M $ET_1$. After 30 min, the free and the bound -radioligand were separated by filtration through GF/B glass fiber filters (Whatman, England) on a Skatron cell collector (Skatron, Lier, Norway) and the filters were washed with ice-cold tris HCl buffer, pH 7.4 with 0.2% BSA.

The radioactivity collected on the filters was quantified using a Packard 2200 CA liquid scintillation counter.

Testing of the ET Antagonists in Vivo:

Male SD rats weighing 250–300 g were anesthetized with amobarbital, artificially ventilated, vagotomized and pithed. The carotid artery and jugular vein were catheterized.

In control animals, the intravenous administration of 1 mg/kg of ET1 leads to a clear blood pressure rise, which lasts for a relatively long period.

The test animals were injected i.v. (1 ml/kg) with the test compounds 30 min before ET1 administration. To determine the ET-antagonistic properties, the blood pressure changes in the test animals were compared with the those in the control animals.

p.o. Testing of the Mixed $ET_A$ and $ET_B$ antagonists:

Male normotonic rats (Sprague Dawley, Janvier) weighing 250–350 g are orally pretreated with the test substances. 80 minutes later, the animals are anesthetized with urethane and the carotid artery is catheterized (for blood pressure measurement) and also the jugular vein (administration of big endothelin/endothelin 1).

After a stabilization phase, big endothelin (20 µg/kg, admr. vol. 0.5 ml/kg) or ET1 (0.3 µg/kg, admr. vol. 0.5 ml/kg) is given intravenously. Blood pressure and heart rate are recorded continuously for 30 minutes. The clear and long-lasting blood pressure changes are calculated as the area under the curve (AUC). To determine the antagonistic action of the test substances, the AUC of the substance-treated animals is compared with the AUC of the control animals.

The compounds according to the invention can be administered orally or parentally (subcutaneously, intravenously, intramuscularly, intraperitoneally) in a customary manner. Administration can also be carried out through the nasopharynx using vapors or sprays.

The dose depends on the age, condition and weight of the patient and also on the manner of administration. As a rule, the daily active compound dose is from approximately 0.5 to 100 mg/kg of body weight in the case of oral administration and from approximately 0.1 to 10 mg/kg of body weight in the case of parenteral administration.

The novel compounds can be administered in solid or liquid form in the conventional pharmaceutical administration forms, e.g. as tablets, film-coated tablets, capsules, powders, granules, coated tablets, suppositories, solutions, ointments, creams or sprays. These are prepared in a customary manner. The active compounds can in this case be processed with the customary pharmaceutical auxiliaries such as tablet binders, fillers, preservatives, tablet disintegrants, flow-regulating agents, plasticizers, wetting agents, dispersants, emulsifiers, solvents, release-delaying agents, antioxidants and/or propellants (cf. H. Sucker et al.: Pharmazeutische Technologie [Pharmaceutical Technology], Thieme-Verlag, Stuttgart, 1991). The application forms thus obtained normally contain the active compound in an amount from 0.1 to 90% by weight.

SYNTHESIS EXAMPLES

Example 1

2-Methylsulfonyl-4,5-dimethylthiazole 2.7 g of 2-methylmercapto-4,5-dimethylthiazole were initially introduced into methylene chloride at ice temperature and 5.9 g of mCPBA were added. The batch was stirred at room temperature for 16 hours and then extracted once with sodium hydrogen-carbonate solution and with sodium thiosulfate solution. The organic phase was dried over magnesium sulfate, the solvent was distilled off and 2.88 g of oil were isolated, which were directly employed further.

$^1$H-NMR (200 MHz): 3.25 ppm (3 H, s), 2.50(3 H, s), 2.40 (3 H, s). ESI-MS: $M^+$=191.

Example 2

2-Methylmercapto-4,5-cyclopentenothiazole 10.4 g of ammonium dithiocarbamate were initially introduced into ethanol and 7.5 g of 2-chlorocyclopentanone were added. After 30 minutes, the reaction was complete and the reaction mixture was added to water. The aqueous phase was rendered strongly alkaline using sodium hydroxide solution, extracted with methylene chloride and then adjusted to pH 2 using concentrated hydrochloric acid. The aqueous phase was extracted with ethyl acetate, the organic phase was dried with magnesium sulfate and the solvent was distilled off. The residue was taken up in toluene, a spatula tipful of p-toluenesulfonic acid was added and the solvent was distilled off at 60° C. 7.9 g of oil were dissolved in 75 ml of water and 2.4 g of NaOH and 5.7 ml of dimethyl sulfate were rapidly added dropwise. After one hour, the reaction was complete and the mixture was added to water. The aqueous phase was extracted with ether, the organic phase was dried with magnesium sulfate and the solvent was distilled off. The residue was employed in the following reaction without further purification.

Example 3

2-Methylsulfonyl-4,5-cyclopentenothiazole 1.9 g of 2-methylmercapto-4,5-cyclopentenothiazole were initially introduced at ice temperature into methylene chloride and 7.3 g of mCPBA were added. The batch was stirred at room temperature for 16 hours and then extracted once with 1 N sodium hydroxide solution and with sodium thiosulfate solution. The organic phase was dried over magnesium sulfate, the solvent was distilled off and 2.25 g of oil were isolated, which were directly employed further.

$^1$H-NMR (200 MHz): 3.26 ppm (3 H, s), 3.05 (2 H, dd), 2.95(2 H, dd), 2.55 (2 H, dddd). ESI-MS: $M^+$=203.

Example 4

2-Methylsulfonyl-4,5-dimethyloxazole 3 g of 2-methylthio-4,5-dimethyloxazole were dissolved in 100 ml of methylene chloride and 13 g of mCPBA were added at ice temperature. The batch was stirred for three hours and then added to sodium thiosulfate solution. It was neutralized with sodium hydrogencarbonate and the product was extracted with methylene chloride. After drying over magnesium sulfate, the solvent was distilled off and 2 g of crude product were isolated, which it was directly possible to employ further.

$^1$H-NMR (200 MHz): 3.30 ppm (3 H, s), 2.35(3 H, s), 2.15 (3 H, s). ESI-MS: $M^+$=175.

Example 5

(S)-2-(4,5-Dimethylthiazol-2-yloxy)-3-methoxy-3,3-diphenyl-propionic Acid (I-1)

320 mg of 55% NaH were added to an initial mixture of 1 g of S-2-hydroxy-3-methoxy-3,3-diphenylpropionic acid in 20 ml of THF/20 ml of DMF and the mixture was stirred for 15 minutes. 700 mg of 2-methylsulfonyl-4,5-dimethylthiazole were added to this mixture and it was stirred at room temperature for 16 hours. The batch was then treated with water, the mixture was acidified with citric acid and the product was extracted with ether. After drying over magnesium sulfate and distilling off the solvent, it was purified chromatographically and the product was crystallized from ether/n-hexane. 522 mg of crystals were isolated.

$^1$H-NMR (200 MHz): 7.35–7.20 ppm (10 H, m), 6.25 (1 H, s), 3.30 (3 H, s), 2.25(3 H, s), 2.20 (3 H, s). ESI-MS: $M^+$=383.

Example 6

2-(4,5-Cyclopentenothiazol-2-yloxy)-3-(2-(3,4-dimethoxyphenyl)-ethoxy)-3,3-diphenylpropionic Acid (I-17)

$^1$H-NMR (200 MHz): 7.30–7.20 ppm (10 H, m), 6.80–6.60 (3 H, m), 6.25 (1 H, s), 3.85 (3 H, s), 3.80 (3 H, s), 3.70–3.40 (2 H, m), 2.9–2.6 (4 H, m), 2.30–2.25 (2 H, m). ESI-MS: $M^+$=545.

2-(4,5-Dimethyloxazol-2-yloxy)-3-(2-(3,4-dimethoxyphenyl)-ethoxy)-3,3-diphenylpropionic Acid (I-15)

$^1$H-NMR (200 MHz): 7.30–7.20 ppm (10 H, m), 6.80–6.60 (3 H, m), 6.00 (1 H, s), 3.85 (3 H, s), 3.80 (3 H, s), 3.70–3.40 (2 H, m), 2.80 (2 H, tr), 2.10 (3 H, s), 1.90 (3 H, s). ESI-MS: $M^+$=517.

(S)-2-(Benzothiazol-2-yloxy)-3-methoxy-3,3-diphenylpropionic Acid (I-6)

$^1$H-NMR (200 MHZ): 7.70–7.50 (2 H, m), 7.35–7.20 (12 H, m), 6.50 (1 H, s), 3.30 (3 H, s). ESI-MS: $M^+$=405.

(S)-2-(4,5-Cyclopentenothiazol-2-yloxy)-3-methoxy-3,3-diphenyl-propionic Acid (I-5)

$^1$H-NMR (200 MHz): 7.50–7.20 ppm (10 H, m), 6.40 (1 H, s), 3.30 (3 H, s), 2.80–2.60 (4 H, m), 2.30 (2 H, m). ESI-MS: $M^+$=395.

(S)-2-(4,5-Dimethyloxazol-2-yloxy)-3-methoxy-3,3-diphenyl-propionic Acid (I-4)

$^1$H-NMR (200 MHz): 7.50–7.20 ppm (10 H, m), 6.10 (1 H, s), 3.25 (3 H, s), 2.1 (3H, s), 1.90 (3 H, S). ESI-MS: $M^+$=367.

2-(4,5-Dimethylthiazol-2-yloxy)-3-(2-(3,4-dimethoxyphenyl)-ethoxy)-3,3-diphenylpropionic Acid (I-13)

$^1$H-NMR (200 MHz): 7.30–7.20 ppm (10 H, m), 6.70–6.50 (3 H, m), 6.20 (1 H, s), 3.90 (3 H, s), 3.85 (3 H, s), 3.70–3.40 (2 H, m), 2.80 (2 H, tr), 2.20 (3 H, s), 1.15 (3 H, s). ESI-MS: $M^+$=533.

The compounds in Table I can be prepared similarly or as described in the general section.

TABLE I

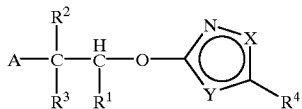

I

| No. | R¹ | R², R³ | A | X | R⁴ | Y |
|---|---|---|---|---|---|---|
| I-1 | COOH | phenyl | MeO | CMe | Me | S |
| I-2 | COOH | 4-Cl-phenyl | MeO | CMe | Me | S |
| I-3 | COOH | 4-F-phenyl | MeO | CMe | Me | S |
| I-4 | COOH | phenyl | MeO | CMe | Me | O |
| I-5 | COOH | phenyl | MeO | C—CH$_2$—CH$_2$—CH$_2$ | | S |
| I-6 | COOH | phenyl | MeO | C—CH=CH—CH=CH | | S |
| I-7 | COOH | phenyl | (4-MeO-phenyl)CH$_2$CH$_2$O | CMe | Me | S |
| I-8 | COOH | phenyl | (4-MeO-phenyl)CH$_2$CH$_2$O | CMe | Me | O |
| I-9 | COOH | 4-F-phenyl | (4-MeO-phenyl)CH$_2$CH$_2$O | CMe | Me | S |
| I-10 | COOH | 4-Cl-phenyl | (4-MeO-phenyl)CH$_2$CH$_2$O | CMe | Me | O |
| I-11 | COOH | phenyl | (4-MeO-phenyl)CH$_2$CH$_2$O | C—CH$_2$—CH$_2$—CH$_2$ | | S |
| I-12 | COOH | phenyl | (4-MeO-phenyl)CH$_2$CH$_2$O | C—CH=CH—CH=CH | | S |
| I-13 | COOH | phenyl | (3,4-DiMeO-phenyl)CH$_2$CH$_2$O | CMe | Me | S |
| I-14 | COOH | 4-F-phenyl | (3,4-DiMeO-phenyl)CH$_2$CH$_2$O | CMe | Me | S |
| I-15 | COOH | phenyl | (3,4-DiMeO-phenyl)CH$_2$CH$_2$O | CMe | Me | O |
| I-16 | COOH | 4-F-phenyl | (3,4-DiMeO-phenyl)CH$_2$CH$_2$O | C—CH$_2$—CH$_2$—CH$_2$ | | S |
| I-17 | COOH | phenyl | (3,4-DiMeO-phenyl)CH$_2$CH$_2$O | C—CH$_2$—CH$_2$—CH$_2$ | | S |
| I-18 | COOH | phenyl | (3,4-DiMeO-phenyl)CH$_2$CH$_2$O | C—CH=CH—CH=CH | | S |
| I-19 | COOH | phenyl | (4-MeO-phenyl)CH$_2$O | CMe | Me | S |
| I-20 | COOH | 4-F-phenyl | (4-MeO-phenyl)CH$_2$O | CMe | Me | S |
| I-21 | COOH | 4-Cl-phenyl | (4-MeO-phenyl)CH$_2$O | CMe | Me | S |
| I-22 | COOH | phenyl | (4-MeO-phenyl)CH$_2$O | CMe | Me | O |
| I-23 | COOH | phenyl | (4-MeO-phenyl)CH$_2$O | C—CH$_2$—CH$_2$—CH$_2$ | | S |
| I-24 | COOH | phenyl | (4-MeO-phenyl)CH$_2$O | C—CH=CH—CH=CH | | S |
| I-25 | COOH | phenyl | (4-MeO-phenyl) O | CMe | Me | S |
| I-26 | COOH | phenyl | (4-MeO-phenyl) O | CMe | Me | O |
| I-27 | COOH | phenyl | (4-MeO-phenyl) O | C—CH$_2$—CH$_2$—CH$_2$ | | S |
| I-28 | COOH | phenyl | (4-MeO-phenyl) O | C—CH=CH—CH=CH | | S |
| I-29 | COOH | phenyl | (3-MeO-4-HO$_2$CCH$_2$O-phenyl)CH$_2$CH$_2$O | CMe | Me | S |
| I-30 | COOH | 4-Cl-phenyl | (3-MeO-4-HO$_2$CCH$_2$O-phenyl)CH$_2$CH$_2$O | CMe | Me | S |
| I-31 | COOH | phenyl | (3-MeO-4-HO$_2$CCH$_2$O-phenyl)CH$_2$CH$_2$O | CMe | Me | O |
| I-32 | COOH | 4-F-phenyl | (3-MeO-4-HO$_2$CCH$_2$O-phenyl)CH$_2$CH$_2$O | C—CH$_2$—CH$_2$—CH$_2$ | | S |
| I-33 | COOH | phenyl | (3-MeO-4-HO$_2$CCH$_2$O-phenyl)CH$_2$CH$_2$O | C—CH$_2$—CH$_2$—CH$_2$ | | S |
| I-34 | COOH | phenyl | (3-MeO-4-HO$_2$CCH$_2$O-phenyl)CH$_2$CH$_2$O | C—CH=CH—CH=CH | | S |
| I-35 | COOH | 4-F-phenyl | (3-MeO-4-Me$_2$NOCCH$_2$O-phenyl)CH$_2$CH$_2$O | CMe | Me | S |
| I-36 | COOH | phenyl | (3-MeO-4-Me$_2$NOCCH$_2$O-phenyl)CH$_2$CH$_2$O | CMe | Me | S |
| I-37 | COOH | phenyl | (3-MeO-4-Me$_2$NOCCH$_2$O-phenyl)CH$_2$CH$_2$O | CMe | Me | O |
| I-38 | COOH | 4-Cl-phenyl | (3-MeO-4-Me$_2$NOCCH$_2$O-phenyl)CH$_2$CH$_2$O | C—CH$_2$—CH$_2$—CH$_2$ | | S |
| I-39 | COOH | phenyl | (3-MeO-4-Me$_2$NOCCH$_2$O-phenyl)CH$_2$CH$_2$O | C—CH$_2$—CH$_2$—CH$_2$ | | S |
| I-40 | COOH | phenyl | (3-MeO-4-Me$_2$NOCCH$_2$O-phenyl)CH$_2$CH$_2$O | C—CH=CH—CH=CH | | S |
| I-41 | COOH | phenyl | (3-MeO-4-Me$_2$NCH$_2$CH$_2$O-phenyl)CH$_2$CH$_2$O | CMe | Me | S |
| I-42 | COOH | 4-F-phenyl | (3-MeO-4-Me$_2$NCH$_2$CH$_2$O-phenyl)CH$_2$CH$_2$O | CMe | Me | S |
| I-43 | COOH | 4-Cl-phenyl | (3-MeO-4-Me$_2$NCH$_2$CH$_2$O-phenyl)CH$_2$CH$_2$O | CMe | Me | S |
| I-44 | COOH | phenyl | (3-MeO-4-Me$_2$NCH$_2$CH$_2$O-phenyl)CH$_2$CH$_2$O | CMe | Me | O |
| I-45 | COOH | phenyl | (3-MeO-4-Me$_2$NCH$_2$CH$_2$O-phenyl)CH$_2$CH$_2$O | C—CH$_2$—CH$_2$—CH$_2$ | | S |
| I-46 | COOH | phenyl | (3-MeO-4-Me$_2$NCH$_2$CH$_2$O-phenyl)CH$_2$CH$_2$O | C—CH=CH—CH=CH | | S |
| I-47 | COOH | phenyl | (4-HO$_2$C-phenyl)CH$_2$CH$_2$O | CMe | Me | S |
| I-48 | COOH | phenyl | (4-HO$_2$C-phenyl)CH$_2$CH$_2$O | CMe | Me | O |
| I-49 | COOH | phenyl | (4-HO$_2$C-phenyl)CH$_2$CH$_2$O | C—CH$_2$—CH$_2$—CH$_2$ | | S |
| I-50 | COOH | phenyl | (4-HO$_2$C-phenyl)CH$_2$CH$_2$O | C—CH=CH—CH=CH | | S |
| I-51 | COOH | phenyl | (4-HO$_2$C-phenyl)CH$_2$O | CMe | Me | S |
| I-52 | COOH | phenyl | (4-HO$_2$C-phenyl)CH$_2$O | CMe | Me | O |
| I-53 | COOH | 4-F-phenyl | (4-HO$_2$C-phenyl)CH$_2$O | C—CH$_2$—CH$_2$—CH$_2$ | | S |
| I-54 | COOH | phenyl | (4-HO$_2$C-phenyl)CH$_2$O | C—CH$_2$—CH$_2$—CH$_2$ | | S |
| I-55 | COOH | phenyl | (4-HO$_2$C-phenyl)CH$_2$O | C—CH=CH—CH=CH | | S |
| I-56 | COOH | phenyl | (4-Me-phenyl)O | CMe | Me | S |
| I-57 | COOH | 4-F-phenyl | (4-Me-phenyl)O | CMe | Me | S |
| I-58 | COOH | 4-Cl-phenyl | (4-Me-phenyl)O | CMe | Me | S |
| I-59 | COOH | phenyl | (4-Me-phenyl)O | CMe | Me | O |
| I-60 | COOH | phenyl | (4-Me-phenyl)O | C—CH$_2$—CH$_2$—CH$_2$ | | S |
| I-61 | COOH | phenyl | (4-Me-phenyl)O | C—CH=CH—CH=CH | | S |
| I-62 | COOH | phenyl | (4-Me-phenyl)CH$_2$O | CMe | Me | S |
| I-63 | COOH | phenyl | (4-Me-phenyl)CH$_2$O | CMe | Me | O |
| I-64 | COOH | phenyl | (4-Me-phenyl)CH$_2$O | C—CH$_2$—CH$_2$—CH$_2$ | | S |
| I-65 | COOH | 4-F-phenyl | (4-Me-phenyl)CH$_2$O | C—CH$_2$—CH$_2$—CH$_2$ | | S |
| I-66 | COOH | phenyl | (4-Me-phenyl)CH$_2$O | C—CH=CH—CH=CH | | S |
| I-67 | COOH | phenyl | (4-Cl-phenyl)CH$_2$CH$_2$O | CMe | Me | S |
| I-68 | COOH | phenyl | (4-Cl-phenyl)CH$_2$CH$_2$O | CMe | Me | O |
| I-69 | COOH | phenyl | (4-Cl-phenyl)CH$_2$CH$_2$O | C—CH$_2$—CH$_2$—CH$_2$ | | S |

TABLE I-continued

I

| No. | R¹ | R², R³ | A | X | R⁴ | Y |
|---|---|---|---|---|---|---|
| I-70 | COOH | phenyl | (4-Cl-phenyl)CH₂CH₂O | C—CH=CH—CH=CH | | S |
| I-71 | COOH | phenyl | (4-Me-phenyl)CH₂CH₂O | CMe | Me | S |
| I-72 | COOH | phenyl | (4-Me-phenyl)CH₂CH₂O | CMe | Me | O |
| I-73 | COOH | phenyl | (4-Me-phenyl)CH₂CH₂O | C—CH₂—CH₂—CH₂ | | S |
| I-74 | COOH | phenyl | (4-Me-phenyl)CH₂CH₂O | C—CH=CH—CH=CH | | S |
| I-75 | COOH | phenyl | (3-HO₂CCH₂O-phenyl)CH₂CH₂O | CMe | Me | S |
| I-76 | COOH | 4-Cl-phenyl | (3-HO₂CCH₂O-phenyl)CH₂CH₂O | CMe | Me | S |
| I-77 | COOH | 4-F-phenyl | (3-HO₂CCH₂O-phenyl)CH₂CH₂O | CMe | Me | S |
| I-78 | COOH | phenyl | (3-HO₂CCH₂O-phenyl)CH₂CH₂O | CMe | Me | O |
| I-79 | COOH | phenyl | (3-HO₂CCH₂O-phenyl)CH₂CH₂O | C—CH₂—CH₂—CH₂ | | S |
| I-80 | COOH | phenyl | (3-HO₂CCH₂O-phenyl)CH₂CH₂O | C—CH=CH—CH=CH | | S |
| I-81 | COOH | phenyl | (3-Me₂NOCCH₂O-phenyl)CH₂CH₂O | CMe | Me | S |
| I-82 | COOH | 4-F-phenyl | (3-Me₂NOCCH₂O-phenyl)CH₂CH₂O | CMe | Me | S |
| I-83 | COOH | 4-Cl-phenyl | (3-Me₂NOCCH₂O-phenyl)CH₂CH₂O | CMe | Me | S |
| I-84 | COOH | phenyl | (3-Me₂NOCCH₂O-phenyl)CH₂CH₂O | CMe | Me | O |
| I-85 | COOH | phenyl | (3-Me₂NOCCH₂O-phenyl)CH₂CH₂O | C—CH₂—CH₂—CH₂ | | S |
| I-86 | COOH | phenyl | (3-Me₂NOCCH₂O-phenyl)CH₂CH₂O | C—CH=CH—CH=CH | | S |
| I-87 | COOH | phenyl | (3-Me₂NCH₂CH₂O-phenyl)CH₂CH₂O | CMe | Me | S |
| I-88 | COOH | phenyl | (3-Me₂NCH₂CH₂O-phenyl)CH₂CH₂O | CMe | Me | O |
| I-89 | COOH | phenyl | (3-Me₂NCH₂CH₂O-phenyl)CH₂CH₂O | C—CH₂—CH₂—CH₂ | | S |
| I-90 | COOH | phenyl | (3-Me₂NCH₂CH₂O-phenyl)CH₂CH₂O | C—CH=CH—CH=CH | | S |
| I-91 | COOH | phenyl | N-Me-N-phenyl-NOCCH₂O | CMe | Me | S |
| I-92 | COOH | 4-F-phenyl | N-Me-N-phenyl-NOCCH₂O | CMe | Me | S |
| I-93 | COOH | 4-Cl-phenyl | N-Me-N-phenyl-NOCCH₂O | CMe | Me | S |
| I-94 | COOH | phenyl | N-Me-N-phenyl-NOCCH₂O | CMe | Me | O |
| I-95 | COOH | phenyl | N-Me-N-phenyl-NOCCH₂O | C—CH₂—CH₂—CH₂ | | S |
| I-96 | COOH | phenyl | N-Me-N-phenyl-NOCCH₂O | C—CH=CH—CH=CH | | S |
| I-97 | COOH | phenyl | N-Bu-N-phenyl-NOCCH₂O | CMe | Me | S |
| I-98 | COOH | 4-F-phenyl | N-Bu-N-phenyl-NOCCH₂O | CMe | Me | S |
| I-99 | COOH | 4-Cl-phenyl | N-Bu-N-phenyl-NOCCH₂O | CMe | Me | S |
| I-100 | COOH | phenyl | N-Bu-N-phenyl-NOCCH₂O | CMe | Me | O |
| I-101 | COOH | phenyl | N-Bu-N-phenyl-NOCCH₂O | C—CH₂—CH₂—CH₂ | | S |
| I-102 | COOH | phenyl | N-Bu-N-phenyl-NOCCH₂O | C—CH=CH—CH=CH | | S |
| I-103 | COOH | phenyl | Bu₂NOCCH₂O | CMe | Me | S |
| I-104 | COOH | phenyl | Bu₂NOCCH₂O | CMe | Me | S |
| I-105 | COOH | 4-F-phenyl | Bu₂NOCCH₂O | CMe | Me | S |
| I-106 | COOH | 4-Cl-phenyl | Bu₂NOCCH₂O | CMe | Me | O |
| I-107 | COOH | phenyl | Bu₂NOCCH₂O | C—CH₂—CH₂—CH₂ | | S |
| I-108 | COOH | phenyl | Bu₂NOCCH₂O | C—CH=CH—CH=CH | | S |
| I-109 | COOH | phenyl | phenyl-HNOCCH₂O | CMe | Me | S |
| I-110 | COOH | 4-Cl-phenyl | phenyl-HNOCCH₂O | CMe | Me | S |
| I-111 | COOH | 4-F-phenyl | phenyl-HNOCCH₂O | CMe | Me | S |
| I-112 | COOH | phenyl | phenyl-HNOCCH₂O | CMe | Me | O |
| I-113 | COOH | phenyl | phenyl-HNOCCH₂O | C—CH₂—CH₂—CH₂ | | S |
| I-114 | COOH | phenyl | phenyl-HNOCCH₂O | C—CH=CH—CH=CH | | S |
| I-115 | COOH | phenyl | (2,6-diethyl-phenyl)-HNOCCH₂O | CMe | Me | S |
| I-116 | COOH | 4-Cl-phenyl | (2,6-diethyl-phenyl)-HNOCCH₂O | CMe | Me | S |
| I-117 | COOH | 4-F-phenyl | (2,6-diethyl-phenyl)-HNOCCH₂O | CMe | Me | S |
| I-118 | COOH | phenyl | (2,6-diethyl-phenyl)-HNOCCH₂O | CMe | Me | O |
| I-119 | COOH | phenyl | (2,6-diethyl-phenyl)-HNOCCH₂O | C—CH₂—CH₂—CH₂ | | S |
| I-120 | COOH | phenyl | (2,6-diethyl-phenyl)-HNOCCH₂O | C—CH=CH—CH=CH | | S |
| I-121 | COOH | phenyl | (—CH₂CH₂CH₂CH₂CH₂CH₂—)NOCCH₂O | CMe | Me | S |
| I-122 | COOH | phenyl | (—CH₂CH₂CH₂CH₂CH₂CH₂—)NOCCH₂O | CMe | Me | O |
| I-123 | COOH | phenyl | (—CH₂CH₂CH₂CH₂CH₂CH₂—)NOCCH₂O | C—CH₂—CH₂—CH₂ | | S |
| I-124 | COOH | phenyl | (—CH₂CH₂CH₂CH₂CH₂CH₂—)NOCCH₂O | C—CH=CH—CH=CH | | S |
| I-125 | COOH | phenyl | (—CH₂CH₂CH₂CH₂—)NOCCH₂O | CMe | Me | S |
| I-126 | COOH | phenyl | (—CH₂CH₂CH₂CH₂—)NOCCH₂O | CMe | Me | O |
| I-127 | COOH | phenyl | (—CH₂CH₂CH₂CH₂—)NOCCH₂O | C—CH₂—CH₂—CH₂ | | S |
| I-128 | COOH | phenyl | (—CH₂CH₂CH₂CH₂—)NOCCH₂O | C—CH=CH—CH=CH | | S |
| I-129 | COOH | phenyl | Me | CMe | Me | S |
| I-130 | COOH | 4-F-phenyl | Me | CMe | Me | S |
| I-131 | COOH | 4-Cl-phenyl | Me | CMe | Me | S |
| I-132 | COOH | phenyl | Me | CMe | Me | O |
| I-133 | COOH | phenyl | Me | C—CH₂—CH₂—CH₂ | | S |
| I-134 | COOH | phenyl | Me | C—CH=CH—CH=CH | | S |
| I-135 | COOH | phenyl | MeS | CMe | Me | S |
| I-136 | COOH | 4-F-phenyl | MeS | CMe | Me | S |
| I-137 | COOH | 4-Cl-phenyl | MeS | CMe | Me | S |
| I-138 | COOH | phenyl | MeS | CMe | Me | O |

TABLE I-continued

| No. | R¹ | R², R³ | A | X | R⁴ | Y |
|---|---|---|---|---|---|---|
| I-139 | COOH | 4-F-phenyl | MeS | C—CH₂—CH₂—CH₂ | | S |
| I-140 | COOH | phenyl | MeS | C—CH₂—CH₂—CH₂ | | S |
| I-141 | COOH | phenyl | MeS | C—CH=CH—CH=CH | | S |
| I-142 | COOH | phenyl | CH₃CONH | CMe | Me | S |
| I-143 | COOH | 4-F-phenyl | CH₃CONH | CMe | Me | S |
| I-144 | COOH | 4-Cl-phenyl | CH₃CONH | CMe | Me | S |
| I-145 | COOH | phenyl | CH₃CONH | CMe | Me | O |
| I-146 | COOH | phenyl | CH₃CONH | C—CH₂—CH₂—CH₂ | | S |
| I-147 | COOH | phenyl | CH₃CONH | C—CH=CH—CH=CH | | S |
| I-148 | COOH | phenyl | (CH₃)₃CCONH | CMe | Me | S |
| I-149 | COOH | 4-F-phenyl | (CH₃)₃CCONH | CMe | Me | S |
| I-150 | COOH | 4-Cl-phenyl | (CH₃)₃CCONH | CMe | Me | S |
| I-151 | COOH | phenyl | (CH₃)₃CCONH | CMe | Me | O |
| I-152 | COOH | phenyl | (CH₃)₃CCONH | C—CH₂—CH₂—CH₂ | | S |
| I-153 | COOH | phenyl | (CH₃)₃CCONH | C—CH=CH—CH=CH | | S |
| I-154 | COOH | phenyl | (—CH₂CH₂—)CHCONH | CMe | Me | S |
| I-155 | COOH | phenyl | (—CH₂CH₂—)CHCONH | CMe | Me | O |
| I-156 | COOH | phenyl | (—CH₂CH₂—)CHCONH | C—CH₂—CH₂—CH₂ | | S |
| I-157 | COOH | phenyl | (—CH₂CH₂—)CHCONH | C—CH=CH—CH=CH | | S |
| I-158 | COOH | phenyl | Et | CMe | Me | S |
| I-159 | COOH | phenyl | Et | CMe | Me | O |
| I-160 | COOH | phenyl | Et | C—CH₂—CH₂—CH₂ | | S |
| I-161 | COOH | phenyl | Et | C—CH=CH—CH=CH | | S |
| I-162 | COOH | phenyl | phenyl-CH₂CH₂S | CMe | Me | S |
| I-163 | COOH | phenyl | phenyl-CH₂CH₂S | CMe | Me | O |
| I-164 | COOH | phenyl | phenyl-CH₂CH₂S | C—CH₂—CH₂—CH₂ | | S |
| I-165 | COOH | phenyl | phenyl-CH₂CH₂S | C—CH=CH—CH=CH | | S |
| I-166 | COOH | phenyl | (4-MeS-phenyl)CH₂CH₂O | CMe | Me | S |
| I-167 | COOH | 4-Cl-phenyl | (4-MeS-phenyl)CH₂CH₂O | CMe | Me | S |
| I-168 | COOH | 4-F-phenyl | (4-MeS-phenyl)CH₂CH₂O | CMe | Me | S |
| I-169 | COOH | phenyl | (4-MeS-phenyl)CH₂CH₂O | CMe | Me | O |
| I-170 | COOH | phenyl | (4-MeS-phenyl)CH₂CH₂O | C—CH₂—CH₂—CH₂ | | S |
| I-171 | COOH | phenyl | (4-MeS-phenyl)CH₂CH₂O | C—CH=CH—CH=CH | | S |
| I-172 | CONHSO₂Me | phenyl | Me | CMe | Me | S |
| I-173 | CONHSO₂Me | 4-F-phenyl | Me | CMe | Me | S |
| I-174 | CONHSO₂Me | 4-Cl-phenyl | Me | CMe | Me | S |
| I-175 | CONHSO₂Me | phenyl | Me | CMe | Me | O |
| I-176 | CONHSO₂Me | phenyl | Me | C—CH₂—CH₂—CH₂ | | S |
| I-177 | CONHSO₂Me | phenyl | Me | C—CH=CH—CH=CH | | S |
| I-178 | CONHSO₂Me | phenyl | (3,4-DiMeO-phenyl)CH₂CH₂O | CMe | Me | S |
| I-179 | CONHSO₂Me | 4-Cl-phenyl | (3,4-DiMeO-phenyl)CH₂CH₂O | CMe | Me | S |
| I-180 | CONHSO₂Me | 4-F-phenyl | (3,4-DiMeO-phenyl)CH₂CH₂O | CMe | Me | S |
| I-181 | CONHSO₂Me | phenyl | (3,4-DiMeO-phenyl)CH₂CH₂O | CMe | Me | O |
| I-182 | CONHSO₂Me | phenyl | (3,4-DiMeO-phenyl)CH₂CH₂O | C—CH₂—CH₂—CH₂ | | S |
| I-183 | CONHSO₂Me | 4-F-phenyl | (3,4-DiMeO-phenyl)CH₂CH₂O | C—CH₂—CH₂—CH₂ | | S |
| I-184 | CONHSO₂Me | phenyl | (3,4-DiMeO-phenyl)CH₂CH₂O | C—CH=CH—CH=CH | | S |
| I-185 | COOH | phenyl | (4-HO-3-MeO-phenyl)CH₂CH₂O | CMe | Me | S |
| I-186 | COOH | phenyl | (4-HO-3-MeO-phenyl)CH₂CH₂O | CMe | Me | O |
| I-187 | COOH | phenyl | (4-HO-3-MeO-phenyl)CH₂CH₂O | C—CH₂—CH₂—CH₂ | | S |
| I-188 | COOH | phenyl | (4-HO-3-MeO-phenyl)CH₂CH₂O | C—CH=CH—CH=CH | | S |
| I-189 | COOH | phenyl | HOCH₂(HOCH)CH₂O | CMe | Me | S |
| I-190 | COOH | 4-F-phenyl | HOCH₂(HOCH)CH₂O | CMe | Me | S |
| I-191 | COOH | 4-Cl-phenyl | HOCH₂(HOCH)CH₂O | CMe | Me | S |
| I-192 | COOH | phenyl | HOCH₂(HOCH)CH₂O | CMe | Me | O |
| I-193 | COOH | phenyl | HOCH₂(HOCH)CH₂O | C—CH₂—CH₂—CH₂ | | S |
| I-194 | COOH | phenyl | HOCH₂(HOCH)CH₂O | C—CH=CH—CH=CH | | S |
| I-195 | COOH | phenyl | HOOCCH₂O | CMe | Me | S |
| I-196 | COOH | phenyl | HOOCCH₂O | CMe | Me | O |
| I-197 | COOH | phenyl | HOOCCH₂O | C—CH₂—CH₂—CH₂ | | S |
| I-198 | COOH | phenyl | HOOCCH₂O | C—CH=CH—CH=CH | | S |
| I-199 | CONHSO₂Me | phenyl | MeO | CMe | Me | S |
| I-200 | CONHSO₂Me | 4-F-phenyl | MeO | CMe | Me | S |
| I-201 | CONHSO₂Me | 4-Cl-phenyl | MeO | CMe | Me | S |
| I-202 | CONHSO₂Me | phenyl | MeO | CMe | Me | O |
| I-203 | CONHSO₂Me | phenyl | MeO | C—CH₂—CH₂—CH₂ | | S |
| I-204 | CONHSO₂Me | phenyl | MeO | C—CH=CH—CH=CH | | S |
| I-205 | COOH | phenyl | (4-EtO-3-MeO-phenyl)CH₂CH₂O | CMe | Me | S |
| I-206 | COOH | phenyl | (4-EtO-3-MeO-phenyl)CH₂CH₂O | CMe | Me | O |
| I-207 | COOH | phenyl | (4-EtO-3-MeO-phenyl)CH₂CH₂O | C—CH₂—CH₂—CH₂ | | |

TABLE I-continued

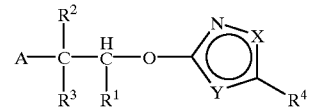

| No. | R¹ | R², R³ | A | X | R⁴ | Y |
|---|---|---|---|---|---|---|
| I-208 | COOH | phenyl | (4-EtO-3-MeO-phenyl)CH$_2$CH$_2$O | C—CH=CH—CH=CH | | S |
| I-209 | COOH | phenyl | EtOOCCH$_2$O | CMe | Me | S |
| I-210 | COOH | phenyl | EIOOCCH$_2$O | CMe | Me | O |
| I-211 | COOH | phenyl | EtOOCCH$_2$O | C—CH$_2$—CH$_2$—CH$_2$ | | S |
| I-212 | COOH | phenyl | EtOOCCH$_2$O | C—CH=CH—CH=CH | | S |
| I-213 | COOH | phenyl | (3-MeO-4-EtO$_2$CCH$_2$O-phenyl)CH$_2$CH$_2$O | CMe | Me | S |
| I-214 | COOH | phenyl | (3-MeO-4-EtO$_2$CCH$_2$O-phenyl)CH$_2$CH$_2$O | CMe | Me | O |
| I-215 | COOH | phenyl | (3-MeO-4-EtO$_2$CCH$_2$O-phenyl)CH$_2$CH$_2$O | C—CH$_2$—CH$_2$—CH$_2$ | | S |
| I-216 | COOH | phenyl | (3-MeO-4-EtO$_2$CCH$_2$O-phenyl)CH$_2$CH$_2$O | C—CH=CH—CH=CH | | S |
| I-217 | COOMe | phenyl | MeO | CMe | Me | S |
| I-218 | COOMe | phenyl | MeO | CMe | Me | O |
| I-219 | COOMe | phenyl | MeO | C—CH$_2$—CH$_2$—CH$_2$ | | S |
| I-220 | COOMe | phenyl | MeO | C—CH=CH—CH=CH | | S |
| I-221 | COOH | phenyl | (4-Me-phenyl)CH$_2$CH$_2$CH$_2$O | CMe | Me | S |
| I-222 | COOH | phenyl | (4-Me-phenyl)CH$_2$CH$_2$O | CMe | Me | O |
| I-223 | COOH | phenyl | (4-Me-phenyl)CH$_2$CH$_2$O | C—CH$_2$—CH$_2$—CH$_2$ | | S |
| I-224 | COOH | phenyl | (4-Me-phenyl)CH$_2$CH$_2$O | C—CH=CH—CH=CH | | S |
| I-225 | COOH | phenyl | (4-MeO-phenyl)CH$_2$CH$_2$CH$_2$O | CMe | Me | S |
| I-226 | COOH | 4-Cl-phenyl | (4-MeO-phenyl)CH$_2$CH$_2$CH$_2$O | CMe | Me | S |
| I-227 | COOH | 4-F-phenyl | (4-MeO-phenyl)CH$_2$CH$_2$CH$_2$O | CMe | Me | S |
| I-228 | COOH | phenyl | (4-MeO-phenyl)CH$_2$CH$_2$CH$_2$O | CMe | Me | O |
| I-229 | COOH | phenyl | (4-MeO-phenyl)CH$_2$CH$_2$CH$_2$O | C—CH$_2$—CH$_2$—CH$_2$ | | S |
| I-230 | COOH | phenyl | (4-MeO-phenyl)CH$_2$CH$_2$CH$_2$O | C—CH=CH—CH=CH | | S |
| I-231 | COOH | phenyl | (4-HOOC-phenyl)CH$_2$CH$_2$CH$_2$O | CMe | Me | S |
| I-232 | COOH | 4-F-phenyl | (4-HOOC-phenyl)CH$_2$CH$_2$CH$_2$O | CMe | Me | S |
| I-233 | COOH | 4-Cl-phenyl | (4-HOOC-phenyl)CH$_2$CH$_2$CH$_2$O | CMe | Me | S |
| I-234 | COOH | phenyl | (4-HOOC-phenyl)CH$_2$CH$_2$CH$_2$O | CMe | Me | O |
| I-235 | COOH | phenyl | (4-HOOC-phenyl)CH$_2$CH$_2$CH$_2$O | C—CH$_2$—CH$_2$—CH$_2$ | | S |
| I-236 | COOH | phenyl | (4-HOOC-phenyl)CH$_2$CH$_2$CH$_2$O | C—CH=CH—CH=CH | | S |
| I-237 | COOH | phenyl | (3,4-DiMeO-phenyl)CH$_2$CH$_2$CH$_2$O | CMe | Me | S |
| I-238 | COOH | 4-F-phenyl | (3,4-DiMeO-phenyl)CH$_2$CH$_2$CH$_2$O | CMe | Me | S |
| I-239 | COOH | 4-Cl-phenyl | (3,4-DiMeO-phenyl)CH$_2$CH$_2$CH$_2$O | CMe | Me | S |
| I-240 | COOH | phenyl | (3,4-DiMeO-phenyl)CH$_2$CH$_2$CH$_2$O | CMe | Me | O |
| I-241 | COOH | 4-F-phenyl | (3,4-DiMeO-phenyl)CH$_2$CH$_2$CH$_2$O | C—CH$_2$—CH$_2$—CH$_2$ | | S |
| I-242 | COOH | phenyl | (3,4-DiMeO-phenyl)CH$_2$CH$_2$CH$_2$O | C—CH$_2$—CH$_2$—CH$_2$ | | S |
| I-243 | COOH | phenyl | (3,4-DiMeO-phenyl)CH$_2$CH$_2$CH$_2$O | C—CH=CH—CH=CH | | S |
| I-244 | COOH | phenyl | (4-Cl-phenyl)CH$_2$CH$_2$O | CMe | Me | S |
| I-245 | COOH | phenyl | (4-Cl-phenyl)CH$_2$CH$_2$O | CMe | Me | O |
| I-246 | COOH | phenyl | (4-Cl-phenyl)CH$_2$CH$_2$O | C—CH$_2$—CH$_2$—CH$_2$ | | S |
| I-247 | COOH | phenyl | (4-Cl-phenyl)CH$_2$CH$_2$O | C—CH=CH—CH=CH | | S |
| I-248 | CONHSO$_2$phenyl | phenyl | MeO | CMe | Me | S |
| I-249 | CONHSO$_2$phenyl | 4-F-phenyl | MeO | CMe | Me | S |
| I-250 | CONHSO$_2$phenyl | 4-Cl-phenyl | MeO | CMe | Me | S |
| I-251 | CONHSO$_2$phenyl | phenyl | MeO | CMe | Me | O |
| I-252 | CONHSO$_2$phenyl | 4-F-phenyl | MeO | C—CH$_2$—CH$_2$—CH$_2$ | | S |
| I-253 | CONHSO$_2$phenyl | 4-Cl-phenyl | MeO | C—CH$_2$—CH$_2$—CH$_2$ | | S |
| I-254 | CONHSO$_2$phenyl | phenyl | MeO | C—CH$_2$—CH$_2$—CH$_2$ | | S |
| I-255 | CONHSO$_2$phenyl | phenyl | MeO | C—CH=CH—CH=CH | | S |
| I-256 | CONHSO$_2$phenyl | phenyl | Me | CMe | Me | S |
| I-257 | CONHSO$_2$phenyl | 4-F-phenyl | Me | CMe | Me | S |
| I-258 | CONHSO$_2$phenyl | 4-Cl-phenyl | Me | CMe | Me | S |
| I-259 | CONHSO$_2$phenyl | phenyl | Me | CMe | Me | O |
| I-260 | CONHSO$_2$phenyl | phenyl | Me | C—CH$_2$—CH$_2$—CH$_2$ | | S |
| I-261 | CONHSO$_2$phenyl | phenyl | Me | C—CH=CH—CH=CH | | S |
| I-262 | CONHSO$_2$phenyl | phenyl | (3,4-DiMeO-phenyl)CH$_2$CH$_2$O | CMe | Me | S |
| I-263 | CONHSO$_2$phenyl | 4-F-phenyl | (3,4-DiMeO-phenyl)CH$_2$CH$_2$O | CMe | Me | S |
| I-264 | CONHSO$_2$phenyl | 4-Cl-phenyl | (3,4-DiMeO-phenyl)CH$_2$CH$_2$O | CMe | Me | S |
| I-265 | CONHSO$_2$phenyl | phenyl | (3,4-DiMeO-phenyl)CH$_2$CH$_2$O | CMe | Me | O |
| I-266 | CONHSO$_2$phenyl | phenyl | (3,4-DiMeO-phenyl)CH$_2$CH$_2$O | C—CH$_2$—CH$_2$—CH$_2$ | | S |
| I-267 | CONHSO$_2$phenyl | phenyl | (3,4-DiMeO-phenyl)CH$_2$CH$_2$O | C—CH=CH—CH=CH | | S |
| I-268 | CONHSO$_2$phenyl | phenyl | N-Me-N-phenyl-NOCCH$_2$O | CMe | Me | S |
| I-269 | CONHSO$_2$phenyl | phenyl | N-Me-N-phenyl-NOCCH$_2$O | CMe | Me | O |
| I-270 | CONHSO$_2$phenyl | phenyl | N-Me-N-phenyl-NOCCH$_2$O | C—CH$_2$—CH$_2$—CH$_2$ | | S |
| I-271 | CONHSO$_2$phenyl | phenyl | N-Me-N-phenyl-NOCCH$_2$O | C—CH=CH—CH=CH | | S |
| I-272 | COOH | phenyl | (4-Me-phenyl)O | CMe | Me | S |
| I-273 | COOH | phenyl | (4-Me-phenyl)O | CMe | Me | O |
| I-274 | COOH | phenyl | (4-Me-phenyl)O | C—CH$_2$—CH$_2$—CH$_2$ | | S |
| I-275 | COOH | phenyl | (4-Me-phenyl)O | C—CH=CH—CH=CH | | S |
| I-276 | COOH | 4-F-phenyl | MeO | S | Me | CH |

TABLE I-continued

| No. | R¹ | R², R³ | A | X | R⁴ | Y |
|---|---|---|---|---|---|---|
| I-277 | COOH | 4-Cl-phenyl | MeO | S | Me | CH |
| I-278 | COOH | phenyl | MeO | O | Me | CMe |
| I-279 | COOH | phenyl | MeO | S | Me | CH |
| I-280 | COOH | phenyl | MeO | O | Me | CH |
| I-281 | COOH | 4-F-phenyl | (4-MeO-phenyl)CH$_2$CH$_2$O | S | Me | CH |
| I-282 | COOH | 4-Cl-phenyl | (4-MeO-phenyl)CH$_2$CH$_2$O | O | Me | CMe |
| I-283 | COOH | 4-Cl-phenyl | (4-MeO-phenyl)CH$_2$CH$_2$O | S | Me | CH |
| I-284 | COOH | phenyl | (4-MeO-phenyt)CH$_2$CH$_2$O | S | Me | CH |
| I-285 | COOH | phenyl | (4-MeO-phenyl)CH$_2$CH$_2$O | O | Me | CH |
| I-286 | COOH | phenyl | (3,4-DiMeO-phenyl)CH$_2$CH$_2$O | S | Me | CH |
| I-287 | COOH | 4-Cl-phenyl | (3,4-DiMeO-phenyl)CH$_2$CH$_2$O | S | Me | CH |
| I-288 | COOH | 4-F-phenyl | (3,4-DiMeO-phenyl)CH$_2$CH$_2$O | S | Me | CH |
| I-289 | COOH | phenyl | (3,4-DiMeO-phenyl)CH$_2$CH$_2$O | O | Me | CMe |
| I-290 | COOH | phenyl | (3,4-DiMeO-phenyl)CH$_2$CH$_2$O | O | Me | CH |
| I-291 | COOH | phenyl | (4-MeO-phenyl)CH$_2$O | S | Me | CH |
| I-292 | COOH | phenyl | (4-MeO-phenyl)CH$_2$O | O | Me | CH |
| I-293 | COOH | phenyl | (4-MeO-phenyl) O | S | Me | CH |
| I-294 | COOH | phenyl | (4-MeO-phenyl) O | O | Me | CH |
| I-295 | COOH | phenyl | (3-MeO-4-HO$_2$CCH$_2$O-phenyl)CH$_2$CH$_2$O | S | Me | CH |
| I-296 | COOH | phenyl | (3-MeO-4-HO$_2$CCH$_2$O-phenyl)CH$_2$CH$_2$O | O | Me | CMe |
| I-297 | COOH | 4-F-phenyl | (3-MeO-4-HO$_2$CCH$_2$O-phenyl)CH$_2$CH$_2$O | S | Me | CH |
| I-298 | COOH | 4-Cl-phenyl | (3-MeO-4-HO$_2$CCH$_2$O-phenyl)CH$_2$CH$_2$O | S | Me | CH |
| I-299 | COOH | phenyl | (3-MeO-4-HO$_2$CCH$_2$O-phenyl)CH$_2$CH$_2$O | O | Me | CH |
| I-300 | COOH | phenyl | (3-MeO-4-Me$_2$NOCCH$_2$O-phenyl)CH$_2$CH$_2$O | S | Me | CH |
| I-301 | COOH | phenyl | (3-MeO-4-Me$_2$NOCCH$_2$O-phenyl)CH$_2$CH$_2$O | O | Me | CMe |
| I-302 | COOH | 4-F-phenyl | (3-MeO-4-Me$_2$NOCCH$_2$O-phenyl)CH$_2$CH$_2$O | S | Me | CH |
| I-303 | COOH | 4-Cl-phenyl | (3-MeO-4-Me$_2$NOCCH$_2$O-phenyl)CH$_2$CH$_2$O | S | Me | CH |
| I-304 | COOH | phenyl | (3-MeO-4-Me$_2$NOCCH$_2$O-phenyl)CH$_2$CH$_2$O | O | Me | CH |
| I-305 | COOH | phenyl | (3-MeO-4-Me$_2$NCH$_2$CH$_2$O-phenyl)CH$_2$CH$_2$O | S | Me | CH |
| I-306 | COOH | phenyl | (4-HO$_2$C-phenyl)CH$_2$CH$_2$O | S | Me | CH |
| I-307 | COOH | phenyl | (4-HO$_2$C-phenyl)CH$_2$CH$_2$O | O | Me | CH |
| I-308 | COOH | phenyl | (4-HO$_2$C-phenyl)CH$_2$O | S | Me | CH |
| I-309 | COOH | phenyl | (4-HO$_2$C-phenyl)CH$_2$O | O | Me | CH |
| I-310 | COOH | phenyl | (4-Me-phenyl)O | S | Me | CH |
| I-311 | COOH | phenyl | (4-Me-phenyl)O | O | Me | CH |
| I-312 | COOH | phenyl | (4-Me-phenyl)CH$_2$O | S | Me | CH |
| I-313 | COOH | phenyl | (4-Me-phenyl)CH$_2$O | O | Me | CH |
| I-314 | COOH | phenyl | (4-Cl-phenyl)CH$_2$O | S | Me | CH |
| I-315 | COOH | phenyl | (4-Cl-phenyl)CH$_2$O | O | Me | CH |
| I-316 | COOH | phenyl | (4-Me-phenyl)CH$_2$CH$_2$O | S | Me | CH |
| I-317 | COOH | phenyl | (4-Me-phenyl)CH$_2$CH$_2$O | O | Me | CH |
| I-318 | COOH | 4-F-phenyl | (3-HO$_2$CCH$_2$O-phenyl)CH$_2$CH$_2$O | S | Me | CH |
| I-319 | COOH | 4-Cl-phenyl | (3-HO$_2$CCH$_2$O-phenyl)CH$_2$CH$_2$O | S | Me | CH |
| I-320 | COOH | phenyl | (3-HO$_2$CCH$_2$O-phenyl)CH$_2$CH$_2$O | O | Me | CMe |
| I-321 | COOH | phenyl | (3-HO$_2$CCH$_2$O-phenyl)CH$_2$CH$_2$O | S | Me | CH |
| I-322 | COOH | phenyl | (3-HO$_2$CCH$_2$O-phenyl)CH$_2$CH$_2$O | O | Me | CH |
| I-323 | COOH | phenyl | (3-Me$_2$NOCCH$_2$O-phenyl)CH$_2$CH$_2$O | S | Me | CH |
| I-324 | COOH | 4-F-phenyl | (3-Me$_2$NOCCH$_2$O-phenyl)CH$_2$CH$_2$O | S | Me | CH |
| I-325 | COOH | 4-Cl-phenyl | (3-Me$_2$NOCCH$_2$O-phenyl)CH$_2$CH$_2$O | S | Me | CH |
| I-326 | COOH | phenyl | (3-Me$_2$NOCCH$_2$O-phenyl)CH$_2$CH$_2$O | O | Me | CMe |
| I-327 | COOH | phenyl | (3-Me$_2$NOCCH$_2$O-phenyl)CH$_2$CH$_2$O | O | Me | CH |
| I-328 | COOH | phenyl | (3-Me$_2$NCH$_2$CH$_2$O-phenyl)CH$_2$CH$_2$O | S | Me | CH |
| I-329 | COOH | phenyl | (3-Me$_2$NCH$_2$CH$_2$O-phenyl)CH$_2$CH$_2$O | O | Me | CH |
| I-330 | COOH | phenyl | N-Me-N-phenyl-NOCCH$_2$O | S | Me | CH |
| I-331 | COOH | 4-F-phenyl | N-Me-N-phenyl-NOCCH$_2$O | S | Me | CH |
| I-332 | COOH | 4-Cl-phenyl | N-Me-N-phenyl-NOCCH$_2$O | S | Me | CH |
| I-333 | COOH | phenyl | N-Me-N-phenyl-NOCCH$_2$O | O | Me | CMe |
| I-334 | COOH | phenyl | N-Me-N-phenyl-NOCCH$_2$O | O | Me | CH |
| I-335 | COOH | phenyl | N-Bu-N-phenyl-NOCCH$_2$O | S | Me | CH |
| I-336 | COOH | phenyl | N-Bu-N-phenyl-NOCCH$_2$O | O | Me | CH |
| I-337 | COOH | phenyl | Bu$_2$NOCCH$_2$O | S | Me | CH |
| I-338 | COOH | 4-F-phenyl | Bu$_2$NOCCH$_2$O | S | Me | CH |
| I-339 | COOH | 4-Cl-phenyl | Bu$_2$NOCCH$_2$O | S | Me | CH |
| I-340 | COOH | phenyl | Bu$_2$NOCCH$_2$O | O | Me | CMe |
| I-341 | COOH | phenyl | Bu$_2$NOCCH$_2$O | O | Me | CH |
| I-342 | COOH | phenyl | phenyl-HNOCCH$_2$O | S | Me | CH |
| I-343 | COOH | phenyl | phenyl-HNOCCH$_2$O | O | Me | CH |
| I-344 | COOH | phenyl | (2,6-diethyl-phenyl)-HNOCCH$_2$O | S | Me | CH |
| I-345 | COOH | 4-F-phenyl | (2,6-diethyl-phenyl)-HNOCCH$_2$O | S | Me | CH |

TABLE I-continued

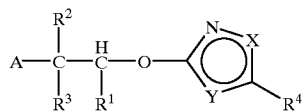

| No. | $R^1$ | $R^2, R^3$ | A | X | $R^4$ | Y |
|---|---|---|---|---|---|---|
| I-346 | COOH | 4-Cl-phenyl | (2,6-diethyl-phenyl)-HNOCCH$_2$O | S | Me | CH |
| I-347 | COOH | phenyl | (2,6-diethyl-phenyl)-HNOCCH$_2$O | O | Me | CMe |
| I-348 | COOH | phenyl | (2,6-diethyl-phenyl)-HNOCCH$_2$O | O | Me | CH |
| I-349 | COOH | phenyl | (—CH$_2$CH$_2$CH$_2$CH$_2$CH$_2$CH$_2$—)NOCCH$_2$O | S | Me | CH |
| I-350 | COOH | phenyl | (—CH$_2$CH$_2$CH$_2$CH$_2$CH$_2$CH$_2$—)NOCCH$_2$O | O | Me | CH |
| I-351 | COOH | phenyl | (—CH$_2$CH$_2$CH$_2$CH$_2$—)NOCCH$_2$O | S | Me | CH |
| I-352 | COOH | phenyl | (—CH$_2$CH$_2$CH$_2$CH$_2$—)NOCCH$_2$O | O | Me | CH |
| I-353 | COOH | phenyl | Me | S | Me | CH |
| I-354 | COOH | 4-F-phenyl | Me | S | Me | CH |
| I-355 | COOH | 4-Cl-phenyl | Me | S | Me | CH |
| I-356 | COOH | phenyl | Me | O | Me | CMe |
| I-357 | COOH | phenyl | Me | O | Me | CH |
| I-358 | COOH | phenyl | MeS | S | Me | CH |
| I-359 | COOH | phenyl | MeS | O | Me | CH |
| I-360 | COOH | phenyl | CH$_3$CONH | S | Me | CH |
| I-361 | COOH | 4-F-phenyl | CH$_3$CONH | S | Me | CH |
| I-362 | COOH | 4-Cl-phenyl | CH$_3$CONH | S | Me | CH |
| I-363 | COOH | phenyl | CH$_3$CONH | O | Me | CMe |
| I-364 | COOH | phenyl | CH$_3$CONH | O | Me | CH |
| I-365 | COOH | phenyl | (CH$_3$)$_3$CCONH | S | Me | CH |
| I-366 | COOH | phenyl | (CH$_3$)$_3$CCONH | O | Me | CH |
| I-367 | COOH | phenyl | (—CH$_2$CH$_2$—)CHCONH | S | Me | CH |
| I-368 | COOH | phenyl | (—CH$_2$CH$_2$—)CHCONH | O | Me | CH |
| I-369 | COOH | phenyl | Et | S | Me | CH |
| I-370 | COOH | phenyl | Et | O | Me | CH |
| I-371 | COOH | phenyl | phenyl-CH$_2$CH$_2$S | S | Me | CH |
| I-372 | COOH | phenyl | phenyl-CH$_2$CH$_2$S | O | Me | CH |
| I-373 | COOH | phenyl | (4-MeS-phenyl)CH$_2$CH$_2$O | S | Me | CH |
| I-374 | COOH | 4-F-phenyl | (4-MeS-phenyl)CH$_2$CH$_2$O | S | Me | CH |
| I-375 | COOH | phenyl | (4-MeS-phenyl)CH$_2$CH$_2$O | O | Me | CMe |
| I-376 | COOH | phenyl | (4-MeS-phenyl)CH$_2$CH$_2$O | O | Me | CH |
| I-377 | CONHSO$_2$Me | phenyl | Me | S | Me | CH |
| I-378 | CONHSO$_2$Me | 4-F-phenyl | Me | S | Me | CH |
| I-379 | CONHSO$_2$Me | 4-Cl-phenyl | Me | S | Me | CH |
| I-380 | CONHSO$_2$Me | phenyl | Me | O | Me | CMe |
| I-381 | CONHSO$_2$Me | phenyl | Me | O | Me | CH |
| I-382 | CONHSO$_2$Me | phenyl | (3,4-DiMeO-phenyl)CH$_2$CH$_2$O | O | Me | CH |
| I-383 | CONHSO$_2$Me | 4-F-phenyl | (3,4-DiMeO-phenyl)CH$_2$CH$_2$O | S | Me | CH |
| I-384 | CONHSO$_2$Me | 4-Cl-phenyl | (3,4-DiMeO-phenyl)CH$_2$CH$_2$O | S | Me | CH |
| I-385 | CONHSO$_2$Me | phenyl | (3,4-DiMeO-phenyl)CH$_2$CH$_2$O | O | Me | CMe |
| I-386 | CONHSO$_2$Me | phenyl | (3,4-DiMeO-phenyl)CH$_2$CH$_2$O | S | Me | CH |
| I-387 | COOH | phenyl | (4-HO-3-MeO-phenyl)CH$_2$CH$_2$O | O | Me | CH |
| I-388 | COOH | 4-F-phenyl | (4-HO-3-MeO-phenyl)CH$_2$CH$_2$O | O | Me | CH |
| I-389 | COOH | 4-Cl-phenyl | (4-HO-3-MeO-phenyl)CH$_2$CH$_2$O | S | Me | CH |
| I-390 | COOH | phenyl | (4-HO-3-MeO-phenyl)CH$_2$CH$_2$O | O | Me | CMe |
| I-391 | COOH | phenyl | (4-HO-3-MeO-phenyl)CH$_2$CH$_2$O | S | Me | CH |
| I-392 | COOH | phenyl | HOCH$_2$(HOCH)CH$_2$O | O | Me | CH |
| I-393 | COOH | phenyl | HOCH$_2$(HOCH)CH$_2$O | S | Me | CH |
| I-394 | COOH | phenyl | HOOCCH$_2$O | O | Me | CH |
| I-395 | COOH | phenyl | HOOCCH$_2$O | S | Me | CH |
| I-396 | CONHSO$_2$Me | phenyl | MeO | O | Me | CH |
| I-397 | CONHSO$_2$Me | 4-F-phenyl | MeO | S | Me | CH |
| I-398 | CONHSO$_2$Me | 4-Cl-phenyl | MeO | S | Me | CH |
| I-399 | CONHSO$_2$Me | phenyl | MeO | O | Me | CMe |
| I-400 | CONHSO$_2$Me | phenyl | MeO | S | Me | CH |
| I-401 | COOH | phenyl | (4-EtO-3-MeO-phenyl)CH$_2$CH$_2$O | O | Me | CH |
| I-402 | COOH | phenyl | (4-EtO-3-MeO-phenyl)CH$_2$CH$_2$O | S | Me | CH |
| I-403 | COOH | phenyl | EtOOCCH$_2$O | O | Me | CH |
| I-404 | COOH | phenyl | EtOOCCH$_2$O | S | Me | CH |
| I-405 | COOH | phenyl | (3-MeO-4-EtO$_2$CCH$_2$O-phenyl)CH$_2$CH$_2$O | O | Me | CH |
| I-406 | COOH | phenyl | (3-MeO-4-EtO$_2$CCH$_2$O-phenyl)CH$_2$CH$_2$O | S | Me | CH |
| I-407 | COOMe | phenyl | MeO | O | Me | CH |
| I-408 | COOMe | 4-Cl-phenyl | MeO | S | Me | CH |
| I-409 | COOMe | 4-F-phenyl | MeO | S | Me | CH |
| I-410 | COOMe | phenyl | MeO | O | Me | CMe |
| I-411 | COOMe | phenyl | MeO | S | Me | CH |
| I-412 | COOH | phenyl | (4-Me-phenyl)CH$_2$CH$_2$CH$_2$O | O | Me | CH |
| I-413 | COOH | phenyl | (4-Me-phenyl)CH$_2$CH$_2$CH$_2$O | S | Me | CH |
| I-414 | COOH | phenyl | (4-MeO-phenyl)CH$_2$CH$_2$CH$_2$O | O | Me | CH |

TABLE I-continued

I $$A-\underset{\underset{R^3}{|}}{\overset{\overset{R^2}{|}}{C}}-\underset{\underset{R^1}{|}}{\overset{\overset{H}{|}}{C}}-O-\text{(ring with N, X, Y, R}^4\text{)}$$

| No. | R¹ | R², R³ | A | X | R⁴ | Y |
|---|---|---|---|---|---|---|
| I-415 | COOH | phenyl | (4-MeO-phenyl)CH₂CH₂CH₂O | S | Me | CH |
| I-416 | COOH | phenyl | (4-HOOC-phenyl)CH₂CH₂CH₂O | O | Me | CH |
| I-417 | COOH | phenyl | (4-HOOC-phenyl)CH₂CH₂CH₂O | S | Me | CH |
| I-418 | COOH | phenyl | (3,4-DiMeO-phenyl)CH₂CH₂CH₂O | O | Me | CH |
| I-419 | COOH | 4-F-phenyl | (3,4-DiMeO-phenyl)CH₂CH₂CH₂O | S | Me | CH |
| I-420 | COOH | 4-Cl-phenyl | (3,4-DiMeO-phenyl)CH₂CH₂CH₂O | S | Me | CH |
| I-421 | COOH | phenyl | (3,4-DiMeO-phenyl)CH₂CH₂CH₂O | O | Me | CMe |
| I-422 | COOH | phenyl | (3,4-DiMeO-phenyl)CH₂CH₂CH₂O | O | Me | CH |
| I-423 | COOH | phenyl | (4-Cl-phenyl)CH₂CH₂CH₂O | S | Me | CH |
| I-424 | COOH | phenyl | (4-Cl-phenyl)CH₂CH₂CH₂O | O | Me | CH |
| I-425 | COOH | phenyl | (4-Me-phenyl)O | S | Me | CH |
| I-426 | COOH | phenyl | (4-Me-phenyl)O | O | Me | CH |
| I-427 | CONHSO₂phenyl | phenyl | MeO | O | Me | CH |
| I-428 | CONHSO₂phenyl | 4-F-phenyl | MeO | S | Me | CH |
| I-429 | CONHSO₂phenyl | 4-Cl-phenyl | MeO | S | Me | CH |
| I-430 | CONHSO₂phenyl | phenyl | MeO | O | Me | CMe |
| I-431 | CONHSO₂phenyl | phenyl | MeO | S | Me | CH |
| I-432 | CONHSO₂phenyl | phenyl | Me | S | Me | CH |
| I-433 | CONHSO₂phenyl | 4-F-phenyl | Me | S | Me | CH |
| I-434 | CONHSO₂phenyl | 4-Cl-phenyl | Me | S | Me | CH |
| I-435 | CONHSO₂phenyl | phenyl | Me | O | Me | CMe |
| I-436 | CONHSO₂phenyl | phenyl | Me | O | Me | CH |
| I-437 | CONHSO₂phenyl | phenyl | (3,4-DiMeO-phenyl)CH₂CH₂O | O | Me | CH |
| I-438 | CONHSO₂phenyl | 4-F-phenyl | (3,4-DiMeO-phenyl)CH₂CH₂O | S | Me | CH |
| I-439 | CONHSO₂phenyl | 4-Cl-phenyl | (3,4-DiMeO-phenyl)CH₂CH₂O | S | Me | CH |
| I-440 | CONHSO₂phenyl | phenyl | (3,4-DiMeO-phenyl)CH₂CH₂O | O | Me | CMe |
| I-441 | CONHSO₂phenyl | phenyl | (3,4-DiMeO-phenyl)CH₂CH₂O | S | Me | CH |
| I-442 | COOH | phenyl | (2,3,4-TriMeO-phenyl)CH₂CH₂O | S | Me | CH |
| I-443 | COOH | 4-F-phenyl | (2,3,4-TriMeo-phenyl)CH₂CH₂O | S | Me | CH |
| I-444 | COOH | 4-Cl-phenyl | (2,3,4-TriMeO-phenyl)CH₂CH₂O | S | Me | CH |
| I-445 | COOH | phenyl | (2,3,4-TriMeO-phenyl)CH₂CH₂O | O | Me | CMe |
| I-446 | COOH | phenyl | (2,3,4-TriMeO-phenyl)CH₂CH₂O | O | Me | CH |
| I-447 | COOH | phenyl | (iPrO-phenyl)CH₂CH₂O | S | Me | CH |
| I-448 | COOH | 4-F-phenyl | (iPrO-phenyl)CH₂CH₂O | S | Me | CH |
| I-449 | COOH | 4-Cl-phenyl | (IPrO-phenyl)CH₂CH₂O | S | Me | CH |
| I-450 | COOH | phenyl | (iPrO-phenyl)CH₂CH₂O | O | Me | CMe |
| I-451 | COOH | phenyl | (iPrO-phenyl)CH₂CH₂O | O | Me | CH |
| I-452 | COOH | phenyl | nbutyl | S | Me | CH |
| I-453 | COOH | 4-F-phenyl | nbutyl | S | Me | CH |
| I-454 | COOH | 4-Cl-phenyl | nbutyl | S | Me | CH |
| I-455 | COOH | phenyl | nbutyl | O | Me | CMe |
| I-456 | COOH | phenyl | nbutyl | O | Me | CH |
| I-457 | COOH | phenyl | (cyclohexyl)CH₂CH₂O | S | Me | CH |
| I-458 | COOH | 4-F-phenyl | (cyclohexyl)CH₂CH₂O | S | Me | CH |
| I-459 | COOH | 4-Cl-phenyl | (cyclohexyl)CH₂CH₂O | S | Me | CH |
| I-460 | COOH | phenyl | (cyclohexyl)CH₂CH₂O | O | Me | CMe |
| I-461 | COOH | phenyl | (cyclohexyl)CH₂CH₂O | O | Me | CH |
| I-462 | COOH | phenyl | (cyclopentyl)CH₂CH₂O | S | Me | CH |
| I-463 | COOH | 4-F-phenyl | (cyclopentyl)CH₂CH₂O | S | Me | CH |
| I-464 | COOH | 4-Cl-phenyl | (cyclopentyl)CH₂CH₂O | S | Me | CH |
| I-465 | COOH | phenyl | (cyclopentyl)CH₂CH₂O | O | Me | CMe |
| I-466 | COOH | phenyl | (cyclopentyl)CH₂CH₂O | O | Me | CH |
| I-467 | COOH | phenyl | CH₂CH₂-Z-CH=CHCH₂CH₂O | S | Me | CH |
| I-468 | COOH | 4-F-phenyl | CH₃CH₂-Z-CH=CHCH₂CH₂O | S | Me | CH |
| I-469 | COOH | 4-Cl-phenyl | CH₃CH₂-Z-CH=CHCH₂CH₂O | S | Me | CH |
| I-470 | COOH | phenyl | CH₃CH₂-Z-CH=CHCH₂CH₂O | O | Me | CMe |
| I-471 | COOH | phenyl | CH₃CH₂-Z-CH=CHCH₂CH₂O | O | Me | CH |
| I-472 | COOH | phenyl | (3,4-dioxomethylenephenyl)CH₂CH₂O | S | Me | CH |
| I-473 | COOH | 4-F-phenyl | (3,4-dioxomethylenephenyl)CH₂CH₂O | S | Me | CH |
| I-474 | COOH | 4-Cl-phenyl | (3,4-dioxomethylenephenyl)CH₂CH₂O | S | Me | CH |
| I-475 | COOH | phenyl | (3,4-dioxomethylenephenyl)CH₂CH₂O | O | Me | CMe |
| I-476 | COOH | phenyl | (3,4-dioxomethylenephenyl)CH₂CH₂O | O | Me | CH |
| I-477 | COOH | phenyl | HOCH₂CH₂ | S | Me | CH |
| I-478 | COOH | 4-F-phenyl | HOCH₂CH₂ | S | Me | CH |
| I-479 | COOH | 4-Cl-phenyl | HOCH₂CH₂ | S | Me | CH |
| I-480 | COOH | phenyl | HOCH₂CH₂ | O | Me | CMe |
| I-481 | COOH | phenyl | HOCH₂CH₂ | O | Me | CH |
| I-482 | COOH | phenyl | (3,5-DiMeO-phenyl)CH₂CH₂O | S | Me | CH |
| I-483 | COOH | 4-F-phenyl | (3,5-DiMeO-phenyl)CH₂CH₂O | S | Me | CH |

TABLE I-continued

I

| No. | R¹ | R², R³ | A | X | R⁴ | Y |
|---|---|---|---|---|---|---|
| I-484 | COOH | 4-Cl-phenyl | (3,5-DiMeO-phenyl)CH₂CH₂O | S | Me | CH |
| I-485 | COOH | phenyl | (3,5-DiMeO-phenyl)CH₂CH₂O | O | Me | CMe |
| I-486 | COOH | phenyl | (3,5-DiMeO-phenyl)CH₂CH₂O | O | Me | CH |
| I-487 | COOH | phenyl | (3,5-DiMeO-phenyl)CH₂CH₂O | CMe | Me | S |
| I-488 | COOH | 4-Cl-phenyl | (3,5-DiMeO-phenyl)CH₂CH₂O | CMe | Me | S |
| I-489 | COOH | 4-F-phenyl | (3,5-DiMeO-phenyl)CH₂CH₂O | CMe | Me | S |
| I-490 | COOH | phenyl | (3,5-DiMeO-phenyl)CH₂CH₂O | CMe | Me | O |
| I-491 | COOH | phenyl | (3,5-DiMeO-phenyl)CH₂CH₂O | C—CH₂—CH₂—CH₂ | Me | S |
| I-492 | COOH | phenyl | HOCH₂CH₂ | CMe | Me | S |
| I-493 | COOH | phenyl | HOCH₂CH₂ | CMe | Me | O |
| I-494 | COOH | 4-F-phenyl | HOCH₂CH₂ | CMe | Me | S |
| I-495 | COOH | 4-Cl-phenyl | HOCH₂CH₂ | CMe | Me | O |
| I-496 | COOH | phenyl | HOCH₂CH₂ | C—CH₂—CH₂—CH₂ | Me | S |
| I-497 | COOH | phenyl | (3,4-dioxomethylenephenyl)CH₂CH₂O | CMe | Me | S |
| I-498 | COOH | 4-F-phenyl | (3,4-dioxomethylenephenyl)CH₂CH₂O | CMe | Me | S |
| I-499 | COOH | phenyl | (3,4-dioxomethylenephenyl)CH₂CH₂O | CMe | Me | O |
| I-500 | COOH | 4-F-phenyl | (3,4-dioxomethylenephenyl)CH₂CH₂O | C—CH₂—CH₂—CH₂ | Me | S |
| I-501 | COOH | phenyl | (3,4-dioxomethylenephenyl)CH₂CH₂O | C—CH₂—CH₂—CH₂ | Me | S |
| I-502 | COOH | phenyl | CH₃CH₂-Z-CH=CHCH₂CH₂O | CMe | Me | S |
| I-503 | COOH | 4-F-phenyl | CH₃CH₂-Z-CH=CHCH₂CH₂O | CMe | Me | S |
| I-504 | COOH | 4-Cl-phenyl | CH₃CH₂-Z-CH=CHCH₂CH₂O | CMe | Me | S |
| I-505 | COOH | phenyl | CH₃CH₂-Z-CH=CHCH₂CH₂O | CMe | Me | O |
| I-506 | COOH | phenyl | CH₃CH₂-Z-CH=CHCH₂CH₂O | C—CH₂—CH₂—CH₂ | Me | S |
| I-507 | COOH | phenyl | (cyclopentyl)CH₂CH₂O | CMe | Me | S |
| I-508 | COOH | phenyl | (cyclopentyl)CH₂CH₂O | CMe | Me | O |
| I-509 | COOH | phenyl | (cyclopentyl)CH₂CH₂O | C—CH₂—CH₂—CH₂ | Me | S |
| I-510 | COOH | phenyl | (cyclopentyl)CH₂CH₂O | C—CH=CH—CH=CH | Me | S |
| I-511 | COOH | phenyl | (cyclohexyl)CH₂CH₂O | CMe | Me | S |
| I-512 | COOH | 4-Cl-phenyl | (cyclohexyl)CH₂CH₂O | CMe | Me | S |
| I-513 | COOH | phenyl | (cyclohexyl)CH₂CH₂O | CMe | Me | O |
| I-514 | COOH | 4-F-phenyl | (cyclohexyl)CH₂CH₂O | C—CH₂—CH₂—CH₂ | Me | S |
| I-515 | COOH | phenyl | (cyclohexyl)CH₂CH₂O | C—CH₂—CH₂—CH₂ | Me | S |
| I-516 | COOH | 4-F-phenyl | n-butyl | CMe | Me | S |
| I-517 | COOH | phenyl | n-butyl | CMe | Me | S |
| I-518 | COOH | phenyl | n-butyl | CMe | Me | O |
| I-519 | COOH | 4-Cl-phenyl | n-butyl | C—CH₂—CH₂—CH₂ | Me | S |
| I-520 | COOH | phenyl | n-butyl | C—CH₂—CH₂—CH₂ | Me | S |
| I-521 | COOH | phenyl | (2,3,4-TriMeO-phenyl)CH₂CH₂O | C—CH=CH—CH=CH | Me | S |
| I-522 | COOH | phenyl | (2,3,4-TriMeO-phenyl)CH₂CH₂O | CMe | Me | S |
| I-523 | COOH | 4-F-phenyl | (2,3,4-TriMeO-phenyl)CH₂CH₂O | CMe | Me | S |
| I-524 | COOH | 4-Cl-phenyl | (2,3,4-TriMeO-phenyl)CH₂CH₂O | CMe | Me | S |
| I-525 | COOH | phenyl | (2,3,4-TriMeO-phenyl)CH₂CH₂O | CMe | Me | O |
| I-526 | COOH | phenyl | (iPrO-phenyl)CH₂CH₂O | C—CH₂—CH₂—CH₂ | Me | S |
| I-527 | COOH | phenyl | (iPrO-phenyl)CH₂CH₂O | CMe | Me | S |
| I-528 | COOH | phenyl | (iPrO-phenyl)CH₂CH₂O | CMe | Me | O |
| I-529 | COOH | phenyl | (iPrO-phenyl)CH₂CH₂O | C—CH₂—CH₂—CH₂ | Me | S |
| I-530 | COOH | phenyl | (iPrO-phenyl)CH₂CH₂O | C—CH=CH—CH=CH | Me | S |
| I-531 | CONHSO₂phenyl | phenyl | MeO | CMe | Me | S |
| I-532 | CONHSO₂phenyl | 4-Cl-phenyl | MeO | CMe | Me | S |
| I-533 | CONHSO₂phenyl | 4-F-phenyl | MeO | CMe | Me | S |
| I-534 | CONHSO₂phenyl | phenyl | MeO | CMe | Me | O |
| I-535 | CONHSO₂phenyl | phenyl | MeO | C—CH₂—CH₂—CH₂ | Me | S |
| I-536 | CONHSO₂phenyl | phenyl | Me | CMe | Me | S |
| I-537 | CONHSO₂phenyl | phenyl | Me | CMe | Me | O |
| I-538 | CONHSO₂phenyl | 4-F-phenyl | Me | CMe | Me | S |
| I-539 | CONHSO₂phenyl | 4-Cl-phenyl | Me | CMe | Me | O |
| I-540 | CONHSO₂phenyl | phenyl | Me | C—CH₂—CH₂—CH₂ | Me | S |
| I-541 | CONHSO₂phenyl | phenyl | (3,4-DiMeO-phenyl)CH₂CH₂O | CMe | Me | S |
| I-542 | CONHSO₂phenyl | 4-F-phenyl | (3,4-DiMeO-phenyl)CH₂CH₂O | CMe | Me | S |
| I-543 | CONHSO₂phenyl | phenyl | (3,4-DiMeO-phenyl)CH₂CH₂O | CMe | Me | O |
| I-544 | CONHSO₂phenyl | 4-F-phenyl | (3,4-DiMeO-phenyl)CH₂CH₂O | C—CH₂—CH₂—CH₂ | Me | S |
| I-545 | CONHSO₂phenyl | phenyl | (3,4-DiMeO-phenyl)CH₂CH₂O | C—CH₂—CH₂—CH₂ | Me | S |
| I-546 | COOH | phenyl, 4-Cl-phenyl | MeO | CMe | Me | S |
| I-547 | COOH | 4-Cl-phenyl, 4-F-phenyl | MeO | CMe | Me | S |
| I-548 | COOH | 4-F-phenyl, phenyl | MeO | CMe | Me | S |
| I-549 | COOH | 4-Me-phenyl, naphthyl | MeO | CMe | Me | O |
| I-550 | COOH | 2-F-phenyl, phenyl | MeO | C—CH₂—CH₂—CH₂ | Me | S |
| I-551 | COOH | 2-F-phenyl, 4-Me-phenyl | MeO | C—CH=CH—CH=CH | Me | S |
| I-552 | COOH | naphthyl, phenyl | (4-MeO-phenyl)CH₂CH₂O | CMe | Me | S |

TABLE I-continued

I

| No. | $R^1$ | $R^2, R^3$ | A | X | $R^4$ | Y |
|---|---|---|---|---|---|---|
| I-553 | COOH | phenyl, 4-Cl-phenyl | $CH_3CH_2O$ | CMe | Me | S |
| I-554 | COOH | 4-Cl-phenyl, 4-F-phenyl | $CH_3CH_2O$ | CMe | Me | S |
| I-555 | COOH | 4-F-phenyl, phenyl | ipropylO | CMe | Me | S |
| I-556 | COOH | naphthyl, naphthyl | MeO | CMe | Me | S |
| I-557 | COOH | naphthyl, naphthyl | MeO | C—$CH_2$—$CH_2$—$CH_2$ | | S |
| I-558 | COOH | 4-F-phenyl, 4-Cl-phenyl | (4-MeO-phenyl)$CH_2CH_2O$ | CMe | Me | O |

Example 7

According to the binding test described above, receptor binding data were measured for the compounds shown below.

The results are shown in Table 2.

Table 2

Receptor binding data ($K_i$ values)

| Compound | $ET_A$ [nM/1] | $ET_B$ [nM/1] |
|---|---|---|
| I-1 | 13 | 650 |
| I-15 | 215 | 485 |
| I-6 | 900 | >7100 |
| I-5 | 50 | >700 |
| I-4 | 29 | 3100 |
| I-13 | 145 | 210 |

We claim:

1. A heterocyclically substituted α-hydroxycarboxylic acid derivative

I where $R^1$ is tetrazole or a group

where R has the following meanings:

a) a radical $OR^5$, where $R^5$ is:
hydrogen, the cation of an alkali metal, the cation of an alkaline earth metal or a physiologically tolerable organic ammonium ion;
$C_3$–$C_8$-cycloalkyl, $C_1$–$C_8$-alkyl, $CH_2$-phenyl, $C_3$–$C_8$-alkenyl, $C_3$–$C_8$-alkynyl or phenyl, in each case unsubstituted or substituted;

b) a five-membered heteroaromatic linked via a nitrogen atom;

c) a group

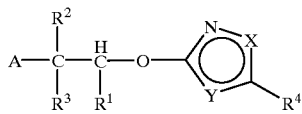

in which k can assume the values 0, 1 or 2, p can assume the values 1, 2, 3 or 4 and $R^6$ is
$C_1$–$C_4$-alkyl, $C_3$–$C_8$-cycloalkyl, $C_3$–$C_8$-alkenyl, $C_3$–$C_8$-alkynyl or unsubstituted or substituted phenyl;

d) a radical

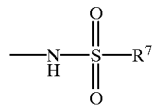

where $R^7$ is:
$C_1$–$C_4$-alkyl, $C_3$–$C_8$-alkenyl, $C_3$–$C_8$-alkynyl, $C_3$–$C_8$-cycloalkyl, it being possible for these radicals to carry a $C_2$–$C_4$-alkoxy, $C_1$–$C_4$-alkylthio and/or a phenyl radical;
$C_1$–$C_4$-haloalkyl or phenyl, which is unsubstituted or substituted;

A is $NR^8R^9$, azido, $OR^{10}$, $SR^{10}$ or $C_1$–$C_4$-alkyl

X is oxygen, sulfur, $CR^{11}$ or $NR^{12}$; with the proviso that if $X=CR^{11}$, then $Y=$oxygen or sulfur or $NR^{14}$;

Y is oxygen, sulfur, $CR^{13}$ or $NR^{14}$; with the proviso that if $Y=$oxygen or sulfur or $NR^{14}$, then $X=CR^{11}$;

$R^2$ and $R^3$ (which can be identical or different):
are phenyl or naphthyl, which is unsubstituted or substituted, or
phenyl or naphthyl, which are connected to one another in the ortho-position via a direct bond, a methylene, ethylene or ethenylene group, an oxygen or sulfur atom or an $SO_2$, NH or N($C_1$–$C_4$-alkyl) group
$C_5$–$C_6$-cycloalkyl, which is unsubstituted or substituted;

$R^4$ and $R^{11}$ (which can be identical or different):
are hydrogen, halogen, $C_1$–$C_4$-alkoxy, $C_1$–$C_4$-haloalkoxy, $C_3$–$C_6$-alkenyloxy, $C_3$–$C_6$-alkynyloxy, $C_1$–$C_4$-alkylthio, $C_1$–$C_4$-alkylcarbonyl, $C_1$–$C_4$-alkoxycarbonyl, hydroxyl, $NH_2$, NH($C_1$–$C_4$-alkyl), N($C_1$–$C_4$-alkyl)$_2$
$C_1$–$C_4$-alkyl, $C_2$–$C_4$-alkenyl, $C_2$–$C_4$-alkynyl, it being possible for these radicals to be unsubstituted or substituted;

or $CR^4$, together with $CR^{11}$, forms a 5- or 6-membered alkylene or alkenylene ring, which can be unsubstituted or substituted, and in which in each case one or more methylene groups can be replaced by oxygen, sulfur, —NH or —N($C_1$–$C_4$-alkyl);

$R^8$ is hydrogen, $C_1$–$C_8$-alkyl, $C_3$–$C_8$-alkenyl, $C_3$–$C_8$-alkynyl, $C_1$–$C_5$-alkylcarbonyl, it being possible for these radicals to be unsubstituted or substituted;

phenyl or naphthyl, which is unsubstituted or substituted;

unsubstituted or substituted $C_3$–$C_8$-cycloalkyl;

or $R^8$, together with $R^9$, forms a $C_3$–$C_7$-alkylene chain, which can be unsubstituted or substituted and is closed to give a ring, and in which an alkylene group can be replaced by oxygen or sulfur;

$R^9$ is hydrogen, $C_1$–$C_4$-alkyl;

or $R^9$ is linked with $R^8$ as indicated under $R^8$ to give a ring;

$R^{10}$ is hydrogen, $C_1$–$C_8$-alkyl, $C_3$–$C_8$-alkenyl, $C_3$–$C_8$-alkynyl, it being possible for these radicals to be unsubstituted or substituted; phenyl or naphthyl, which is unsubstituted or substituted;

unsubstituted or substituted $C_3$–$C_8$-cycloalkyl;

$R^{12}$ is hydrogen, $C_1$–$C_4$-alkyl;

or $NR^{12}$, together with $CR^4$, forms a 5- or 6-membered alkylene or alkenylene ring, which can be unsubstituted or substituted, and in which in each case one or more methylene groups can be replaced by oxygen or sulfur;

$R^{13}$ is hydrogen, halogen, $C_1$–$C_4$-alkyl, $C_2$–$C_4$-alkenyl, $C_2$–$C_4$-alkynyl, it being possible for these radicals to be unsubstituted or substituted;

$R^{14}$ is hydrogen, $C_1$–$C_4$-alkyl;

and the physiologically tolerable salts, and the possible enantiomerically pure and diastereoisomerically pure forms.

2. The method of claim 1, which is a method for treating chronic cardiac insufficiency, restenosis, high blood pressure, high pulmonary pressure, acute/chronic kidney failure, cerebral ischemia, asthma, benign prostate hyperplasia or prostate cancer.

3. A combination of heterocyclically substituted α-hydroxycarboxylic acid derivatives I as claimed in claim 1 and one or more active compounds selected from inhibitors of the renin-angiotensin system such as renin inhibitors, angiotensin II antagonists, angiotensin-converting enzyme (ACE) inhibitors, mixed ACE/neutral endopeptidase (NEP) inhibitors, β-blockers, diuretics, calcium antagonists and VEGF-blocking substances.

4. A pharmaceutical preparation for oral and parenteral use, comprising per individual dose, in addition to the customary drug auxiliaries, at least one carboxylic acid derivative I as claimed in claim 1.

5. A method of inhibiting the binding of endothelin to endothelin receptors in a subject in need of such inhibition, which comprises administering to said subject an effective amount of at least one of the heterocyclically substituted α-hydroxycarboxylic acid derivatives of claim 1.

* * * * *